(12) United States Patent
Hsiue et al.

(10) Patent No.: US 8,299,178 B2
(45) Date of Patent: Oct. 30, 2012

(54) STABLE MICELLES FORMED WITH DIBLOCK COPOLYMERS OF CRITICAL MICELLE CONCENTRATION COPOLYMER AND TEMPERATURE-SENSITIVE COPOLYMER

(75) Inventors: Ging-Ho Hsiue, Hsinchu (TW);
Chun-Liang Lo, Hsinchu (TW);
Sheng-Jie Lin, Hsinchu (TW);
Hsieh-Chih Tsai, Hsinchu (TW)

(73) Assignee: National Tsing Hua University, Hsinchu (TW)

( * ) Notice: Subject to any disclaimer, the term of this patent is extended or adjusted under 35 U.S.C. 154(b) by 676 days.

(21) Appl. No.: 12/411,267

(22) Filed: Mar. 25, 2009

(65) Prior Publication Data
US 2010/0247654 A1 Sep. 30, 2010

(51) Int. Cl.
*A61K 9/14* (2006.01)
*A61K 31/74* (2006.01)

(52) U.S. Cl. .................. 525/92 A; 424/78.08; 424/487; 424/489; 525/90; 525/91; 525/92 F; 525/92 L

(58) Field of Classification Search ................... None
See application file for complete search history.

(56) References Cited

U.S. PATENT DOCUMENTS

2007/0224241 A1* 9/2007 Stayton et al. ................ 424/423
* cited by examiner

*Primary Examiner* — Ana Woodward
(74) *Attorney, Agent, or Firm* — Occhiuti Rohlicek & Tsao LLP

(57) ABSTRACT

A novel class of mixed micelles formed with critical micelle concentration (Cmc) character's diblock copolymer, and temperature-sensitive character's diblock copolymer were disclosed. The mixed micelles possess complementary effects in adjusting external temperature shift (storage vs. body temperature) and concentration change (dilution after intravenous injection). The mixed micelles of the present invention can serve as a potential injectable drug delivery system for anticancer drugs, such as doxorubicin and many others.

11 Claims, 15 Drawing Sheets

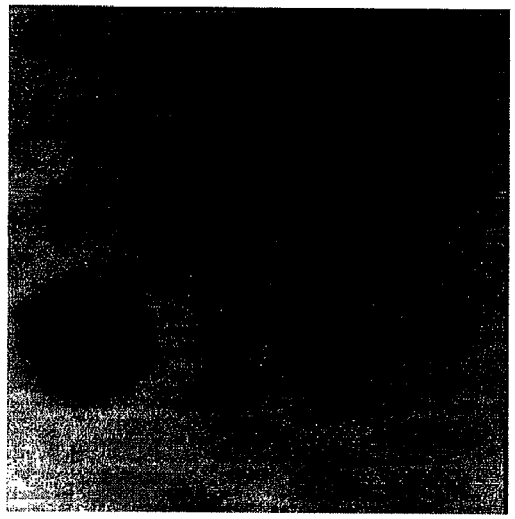 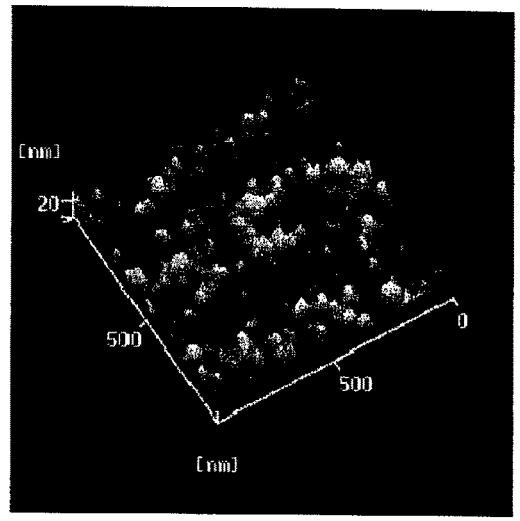
Fig. 12a             Fig. 12b
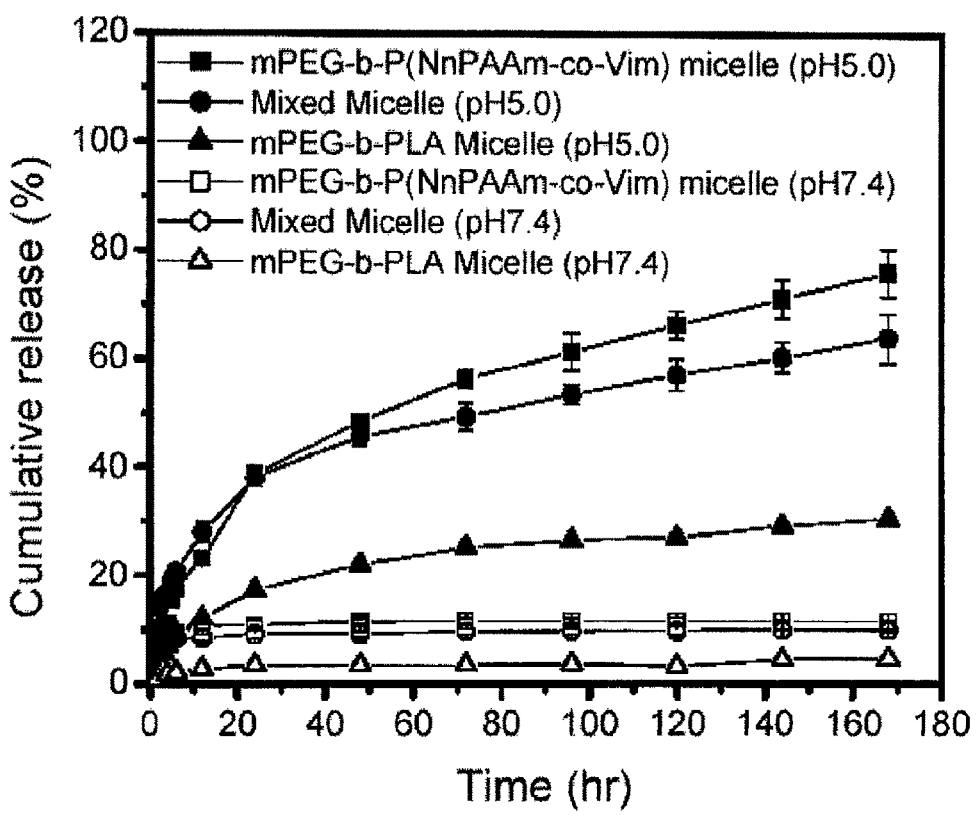
Fig. 13

STABLE MICELLES FORMED WITH DIBLOCK COPOLYMERS OF CRITICAL MICELLE CONCENTRATION COPOLYMER AND TEMPERATURE-SENSITIVE COPOLYMER

FIELD OF THE INVENTION

The present invention is related to a novel class of mixed micelles formed with critical micelle concentration (Cmc) character's diblock copolymer, and temperature-sensitive character's diblock copolymer, and is also related to their use as a potential injectable drug delivery system for anticancer drugs, such as doxorubicin and many others.

BACKGROUND OF THE INVENTION

Micelles formed by diblock copolymers with critical micelle concentration (Cmc) character have been widely investigated for biomedical applications. For anticancer drug delivery, micelles could be roughly divided into two categories based on the drug loading forms. The first category is that micelles consist of polymer-drug conjugates. This kind of micelles guesses more stabile in circulation because almost anticancer drugs are insoluble. The other category is micelles encapsulated drug by physically hydrophobic interaction. However, some of this type of micelles cannot maintain their integral structures due to dramatic dilution after intravenous injection [1]. Several strategies were proposed to overcome such stability problem. For example, micellar structure was strengthen by crosslinking the core and/or shell regions [2,3] and by mixing a crystalline copolymer and a copolymer with lower Cmc to prevent any copolymer dissociation from micelles [4-6].

A portion of Cmc diblock copolymers that with conspicuous temperature-sensitive character, especially for lower critical concentration temperature (LCST) have attracted significant interest continually because of their phase-transition properties, self-assembling to well-established core-shell micelle structure, and wide-ranging applications [7-11]. However, the studies of temperature-sensitive copolymers for drug delivery in vivo are limited, only in the areas of intramuscular or intraperitoneal injection [12,13]. Several critical issues prohibited their broad uses in drug delivery under micelle type. The major problem of temperature-sensitive diblock copolymers is biocompatibility. Most of the temperature-sensitive copolymers are not approved in vivo used. Second, drug release mechanism from temperature-sensitive diblock copolymer-forming micelles is difficult to control due to their phase-transition temperature. Furthermore, poor micellar stability causes serious drug safety issue in clinical application. The above-mentioned problems hinder temperature-sensitive diblock copolymer-forming micelles from gaining significant progress in biomedical applications, especially in intracellular drug delivery.

US patent publication No. 2008/081075 A1 discloses a mixed micelle structure with a functional inner core and hydrophilic outer shell self-assembled from a graft macromolecule and one or more block copolymer, and preferably from a graft copolymer and two or more diblock copolymers. Said graft macromolecule comprising a backbone and hydrophobic side chains bound to the backbone, said block copolymer comprising a hydrophobic polymeric segment and a hydrophilic polymeric segment, wherein the hydrophobic side chains of said graft macromolecule are aggregated, and the hydrophobic polymeric segment of said block polymer is packed and associated to the aggregated hydrophobic side chains of the graft macromolecule with the hydrophilic polymeric segment of the block polymer extruding therefrom to form the core-shell structure. This mixed micelle forms a micellar solution in an aqueous medium, which is temperature sensitive and pH sensitive. Preferably, a terminal functionality is connected to an end of the hydrophilic polymeric segment of said block copolymer, and said terminal functionality is a ligand able to be bound to a receptor on a surface of a tumor cell, a fluorescence group or a dye, so that the mixed micelle is suitable for use as a cancer diagnosis agent and a cancer hydrophobic drug delivery carrier. The disclosure of US patent publication No. 2008/081075 A1 is incorporated herein by reference.

SUMMARY OF THE INVENTION

In the present invention, a new class of polymeric micelles comprising a temperature-sensitive block copolymer were synthesized to resolve some of the above-mentioned drawbacks in the prior art. Said temperature-sensitive block copolymer comprises a hydrophobic polymeric segment and a hydrophilic polymeric segment, wherein said hydrophobic polymeric segment is a copolymer of monomers comprising a pH-/ionic strength sensitive monomer and a temperature-sensitive monomer, wherein the polymeric micelle has a LCST lower than 37° C. at a pH value of 7-8 and has a LCST greater than 37° C. at a pH value of 6 or less than 6; the polymeric micelle has a polydispersity index less than 0.2; and the polymeric micelle forms a micellar solution in water with micellar particle sizes within 50-200 nm. Said hydrophilic polymeric segment of the temperature-sensitive block copolymer renders the polymeric micelle amphiphilic as temperature higher than LCST, and the micellar solution formed is more stable and the micellar particles are smaller in size in comparison with the polymeric micelle composed of only the hydrophobic polymeric segment. The hydrophilic polymeric segment of the temperature-sensitive block copolymer also plays a protection roll in the polymeric micelle of the present invention after intravenous injection into the blood circulation.

In one of the preferred embodiments of the present invention, a new class of mixed micelles comprising a temperature-sensitive diblock copolymer and a Cmc diblock copolymer were synthesized. The physicochemical studies of this new class of mixed micelles show that they possess complementary effects in adjusting external environmental changes, such as temperature and concentration. With these unique characters, the mixed micelles of the present invention formed with the temperature-sensitive diblock copolymer and Cmc diblock copolymer can significantly improve their stability under various physiological conditions.

Preferably, said pH-/ionic strength sensitive monomer is acrylic acid, methacrylic acid, butenedioic acid, amino acid, or vinylimidazole. More preferably, said pH-/ionic strength sensitive monomer is histidine or vinylimidazole. Most preferably, said pH-/ionic strength sensitive monomer is vinylimidazole.

Preferably, said temperature-sensitive monomer is N-isopropyl acrylamide or N-n-propyl acrylamide. In one of the preferred embodiments of the present invention said temperature-sensitive monomer is N-n-propyl acrylamide.

Preferably, said temperature-sensitive block copolymer is diblock copolymer.

Preferably, said hydrophilic polymeric segment of the block copolymer is a homopolymer or copolymer of monomer selected from the group consisting of (meth)acrylic acid, acrylamide, vinylpyrrolidone, saccharide, amino acid, and ethylene oxide.

Preferably, said hydrophilic polymeric segment of the block copolymer is poly(ether), poly(alkylene oxide), poly (alkylene oxide) with terminal C1-C6 alkyl ether, or poly(2-ethyl-2-oxazoline). More preferably, said hydrophilic polymeric segment of the block copolymer is methoxy-poly (ethylene glycol).

Preferably, said hydrophobic polymeric segment of the block copolymer has a number-average molecular weight of 500-2500, and said hydrophilic polymeric segment of the block copolymer has a number-average molecular weight of 2000-20000.

Preferably, the polymeric micelle of the present invention is a mixed micelle further comprising a Cmc block copolymer, wherein said Cmc block copolymer comprises a hydrophobic polymeric segment, and a hydrophilic polymeric segment.

Preferably, said Cmc block copolymer is diblock copolymer, and a weight ratio of said temperature-sensitive block copolymer to said Cmc diblock copolymer ranges from 99:1 to 25:75.

Preferably, said Cmc block copolymer has a Cmc value of $1 \times 10^{-3}$ to $1 \times 10^{-6}$ mg/mL.

Preferably, the mixed micelle has a LCST lower than 25° C. at a pH value of 7-8; and the mixed micelle forms a micellar solution in water with particle size within 80-150.

Preferably, said hydrophilic polymeric segment of the Cmc block copolymer is a homopolymer or copolymer of monomer selected from the group consisting of (meth)acrylic acid, acrylamide, vinylpyrrolidone, saccharide, amino acid, and ethylene oxide.

Preferably, said hydrophilic polymeric segment of the Cmc block copolymer is poly(ether), poly(alkylene oxide), poly (alkylene oxide) with terminal C1-C6 alkyl ether, or poly(2-ethyl-2-oxazoline). More preferably, said hydrophilic polymeric segment of the Cmc block copolymer is methoxy-poly (ethylene glycol).

Preferably, the hydrophobic polymeric segment of the Cmc block copolymer is bioresorable.

Preferably, the hydrophobic polymer segment of the Cmc block copolymer is poly(ester), poly(lactide), poly(lactic acid), or polycaprolactone. More preferably, the hydrophobic polymer segment of the block copolymer is poly(lactide).

Preferably, said hydrophobic polymeric segment of the Cmc block copolymer has a number-average molecular weight of 500-2500, and said hydrophilic polymeric segment of the Cmc block copolymer has a number-average molecular weight of 2000-20000.

Preferably, a molar ratio of said pH-/ionic strength sensitive monomer to said temperature-sensitive monomer in said hydrophobic polymeric segment of the copolymer ranges from 1:99 to 25:75.

Preferably, said temperature-sensitive diblock copolymer is methoxy-poly(ethylene glycol)-b-poly(N-n-propyl acrylamide-co-vinylimidazole).

Preferably, said Cmc diblock copolymer is methoxy-poly (ethylene glycol)-b-poly(D,L-lactide).

Preferably, the Cmc block copolymer has a terminal functionality connected to an end of the hydrophilic polymeric segment thereof, and said terminal functionality is a ligand able to be bound to a receptor on a surface of a tumor cell, a fluorescence group or a dye.

The present invention also provides a drug-loaded micelle comprising the polymeric micelle of the present invention, and a hydrophobic drug enclosed in the polymeric micelle.

Preferably, the drug-loaded micelle comprises the mixed micelle of the present invention.

A suitable process for preparing the polymeric micelle of the present invention comprises the following steps:

a) dissolving a temperature-sensitive block copolymer and optionally a Cmc block copolymer in an organic solvent, wherein said temperature-sensitive block copolymer comprising a hydrophobic polymeric segment and a hydrophilic polymeric segment, wherein said hydrophobic polymeric segment is a copolymer of monomers comprising a pH-/ionic strength sensitive monomer and a temperature-sensitive monomer, and said Cmc block copolymer comprises a hydrophobic polymeric segment and a hydrophilic polymeric segment;

b) mixing the resulting polymer solution from step a) with an aqueous medium having a temperature higher than LCST of said temperature-sensitive block copolymer to form a micellar solution in the aqueous medium; and c) subjecting the resulting mixture from step b) to a dialysis treatment against water to replace the organic solvent in the mixture with water or subjecting the resulting mixture from step b) to a reduced pressure and/or an elevated temperature to evaporate the organic solvent from the mixture.

Preferably, the process of the present invention further comprises d) freeze-drying the resulting aqueous micellar solution from step c) to obtain dried polymeric micelle.

Preferably, the process of the present invention, prior to step b), further comprises mixing an organic solution of a hydrophobic drug or mixing a hydrophobic drug with the resulting polymer solution from step a).

Preferably, said Cmc block copolymer is dissolved in the organic solvent together with the temperature-sensitive block copolymer in step a) of the process of the present invention.

Preferably, the process of the present invention, prior to step b), further comprises mixing an organic solution of a hydrophobic drug or mixing a hydrophobic drug with the resulting polymer solution from step a).

BRIEF DESCRIPTION OF THE DRAWINGS

FIGS. 10a and FIG. 10c are the particles sizes. FIG. 10b and FIG. 10d are the particle size distributions. For the effect of temperature changes on micelles, the concentration of micelles in PBS was ca. 10 mg/mL. For the effect of concentration changes on micelles, the temperature of micellar solutions is fixed at 37° C. The correlation functions from DLS were analyzed by the constrained regularized CONTIN method. The PI means the second moment of the cumulant analysis from DLS. Mean±sd (n=3).

FIG. 12a and FIG. 12b show TEM images of and AFM images of Dox-mixed micelles, respectively.

FIG. 13 shows Dox release behavior from Dox-mPEG-b-PLA micelles, Dox-mPEG-b-P(NnPAAm-co-VIm) micelles, and Dox-mixed micelles under acidic and neutral conditions (Mean±sd (n=3)).

DETAILED DESCRIPTION OF THE INVENTION

Figure 1:
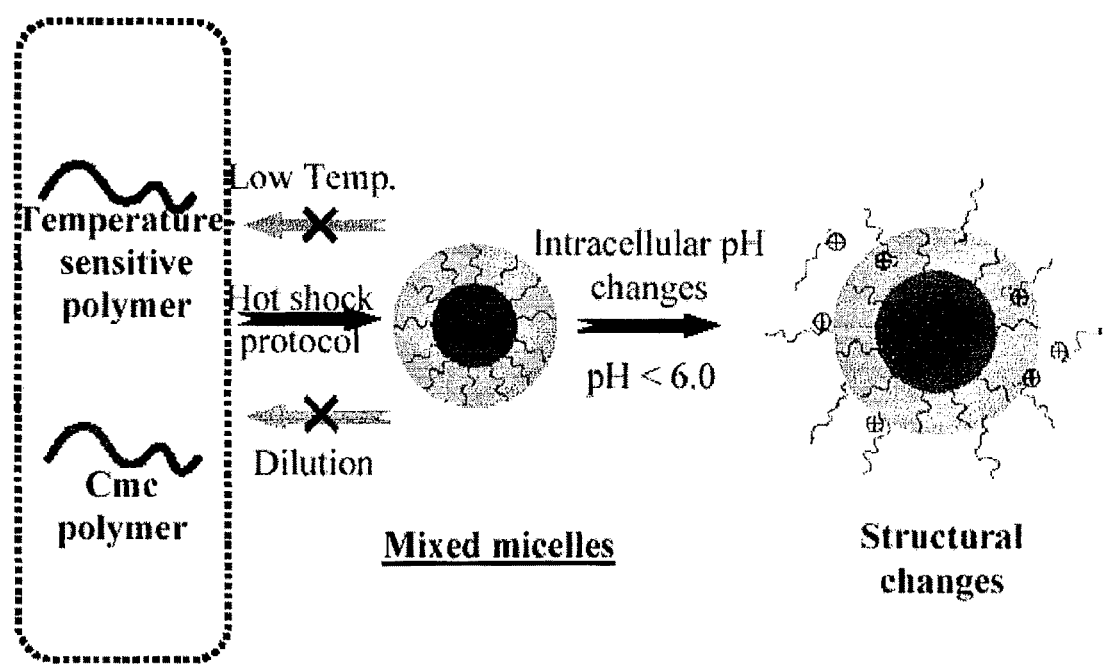
FIG. 1 is a schematic representation of the concept for designing a mixed micelle composed of mPEG-b-PLA and mPEG-b-P(NnPAAm-co-VIm) diblock copolymers according to one of the preferred embodiments of the present invention and its extending application in intracellular drug delivery. (Diagrams depict speculated structural changes of mixed micelles.)

The newly-developed mixed micelle system disclosed in the present invention, which is different from published mixed micelles and those of our previous studies, is schematically illustrated in FIG. 1. The new class of mixed micelles includes a biocompatible Cmc diblock copolymer, methoxy poly(ethylene glycol)-block-poly(D,L-lactide) (mPEG-b-PLA) and a temperature-sensitive diblock copolymer, methoxy poly(ethylene glycol)-block-poly(N-n-propylacrylamide-co-vinylimidazole) (mPEG-b-P(NnPAAm-co-VIm)). The temperature-sensitive diblock copolymer, mPEG-b-P(NnPAAm-co-VIm), is thermo-reversible and is soluble in aqueous solution when temperature is below its cloud point but can self-aggregate to form micelles above its cloud point (certainly also above its Cmc). The conformation change of mPEG-b-P(NnPAAmco-VIm) in association with temperature can affect micellar structure and stability. For example, it maintains as a soluble form during storage (at temperature below its cloud point) and forms micelles to protect drug molecules after intravenous injection (ca. 37° C., temperature above its cloud point). To improve micellar stability of the temperature-sensitive diblock copolymers, a Cmc diblock copolymer, mPEG-b-PLA was introduced into micellar structure to hinder the mobility of the temperature-sensitive diblock copolymers, even at temperature below cloud point of mPEG-b-P(NnPAAm-co-Vim). Furthermore, mixing the temperature-sensitive diblock copolymers with mPEG-b-PLA copolymers could also abridge the disintegration of mPEG-b-PLA when they were diluted into the blood stream due to the body temperature is above the cloud point of mPEG-b-P(NnPAAm-co-VIm). To the best of our knowledge, the present invention presents the first example of a novel micellar structure formed by a temperature-sensitive diblock copolymer and a Cmc diblock copolymer in order to compensate each other to provide excellent micellar stability under various physiological conditions. Therefore, it can be practically applied to intravenous drug delivery for many potent but toxic drugs, such as anticancer drugs.

EXAMPLES

Materials and Methods.
Synthesis of mPEG-b-PLA Diblock Copolymer.

mPEG-b-PLA diblock copolymer was synthesized by ring-opening polymerization. D,L-Lactide (1 g), mPEG (Mw=5000 Da) (10 g) and toluene (4 mL) were added to a two-necked round-bottle flask with a magnetic stirring bar. The mixture was heated in an oil bath and stirred at 130° C. under nitrogen. Stannous octoate (1 wt %) was then added to start the polymerization, which was continued for 16 h at 130° C. After polymerization, the product was terminated by adding 0.1 N methanolic KOH and recrystallizing from dichloromethane and diethyl ether cosolvent at −20° C. mPEG-b-PLA ([EG]:[LA]=113:7 mol/mol) was thus obtained.

Figure 2:
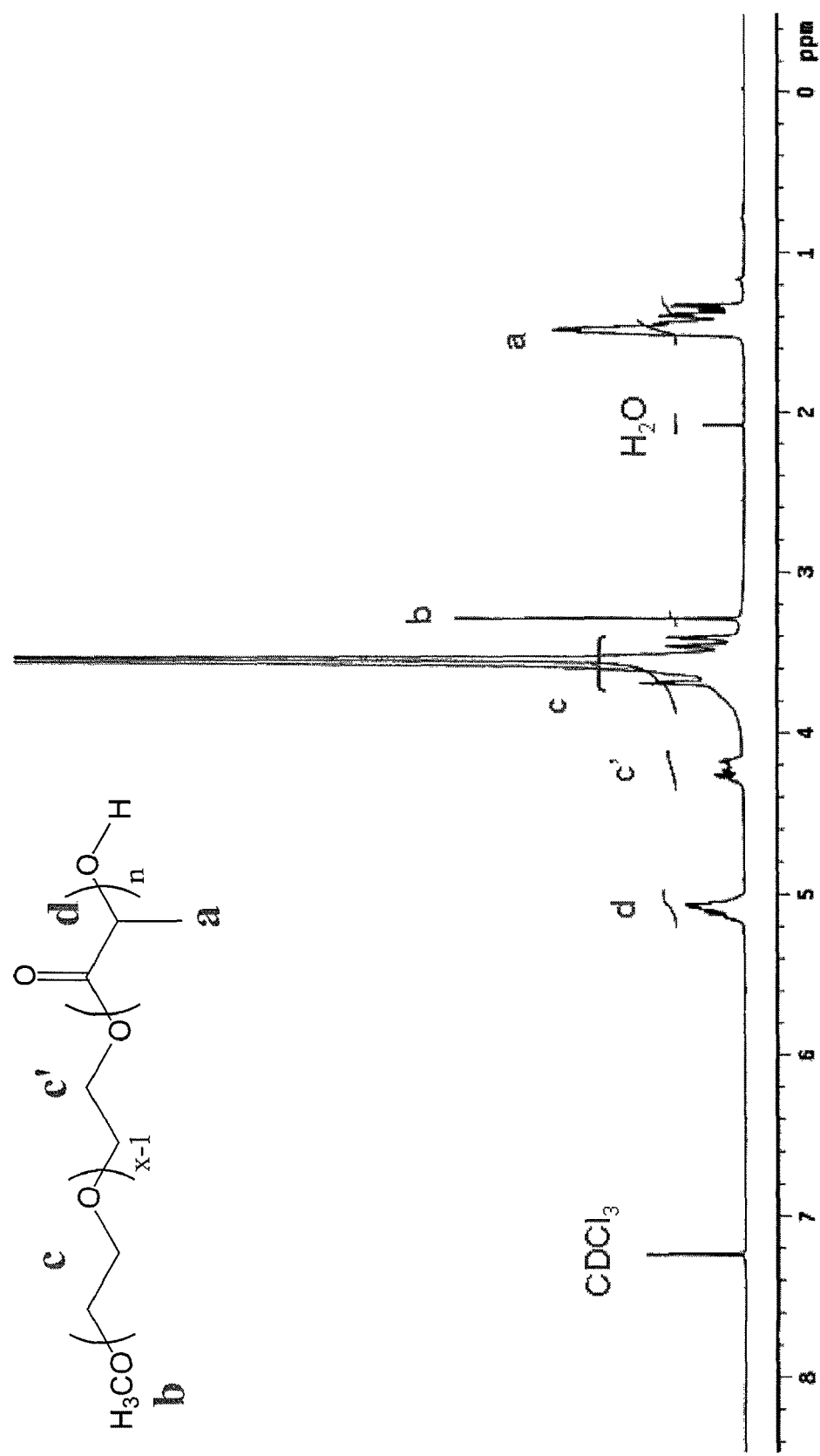
FIG. 2 shows $^1$H-NMR spectrum of mPEG-b-PLA diblock copolymer.
Figure 3:
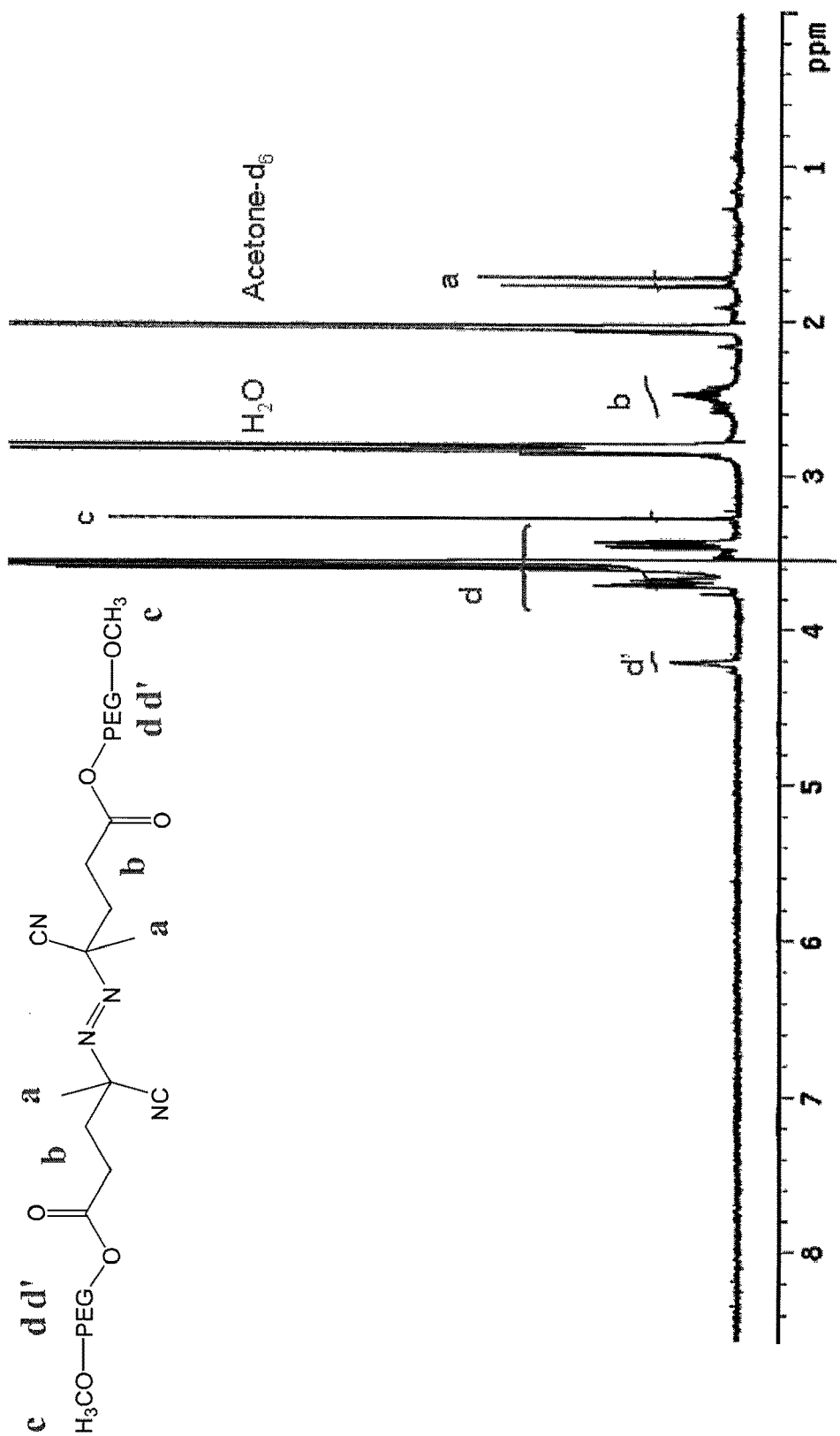
FIG. 3 shows $^1$H-NMR spectrum of mPEG2-ABCPA.
Figure 4:
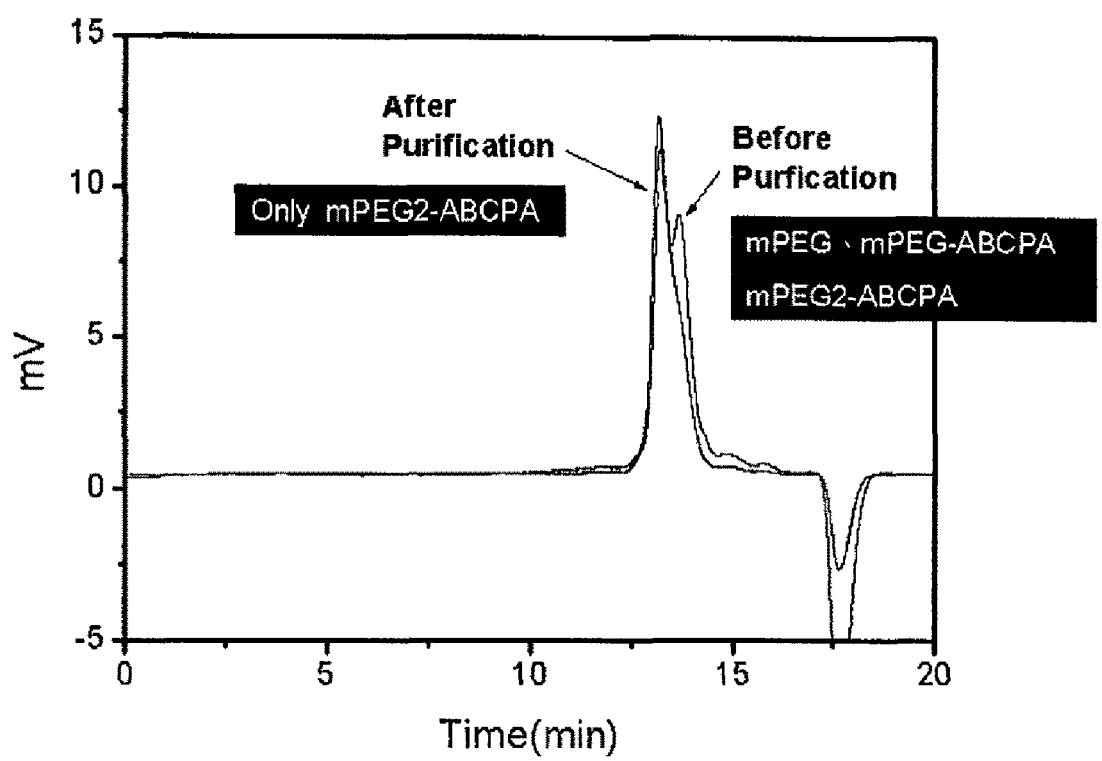
FIG. 4 shows GPC analysis of mPEG2-ABCPA.

The chemical structure of mPEG-b-PLA was characterized by 1H-NMR (AMX-500, Bruker), which is shown in FIG. 2. Additionally, the polydispersity index (PI) was 1.2 from GPC determination. The number average molecular weight of mPEG is 5 kg/mol, and is 1.75 kg/mol for PLA.
Synthesis of mPEG2-ABCPA Macroinitiator.

mPEG (2 mmol) with Mw 5000, 4,4'-azobis-(4-cyanopentanoic acid) (ABCPA, 1 mmol), and of 4-(dimethylamino) pyridinium-4-toluenesulfonate (DPTS, 0.3 mmol) [20] were dissolved in dry dichloromethane and added to a two-necked round-bottle flask with a magnetic stirred and an addition funnel. N,N'-Dicyclohexyl carbodiimide (DCC, 3 mmol) was dissolved in dry dichloromethane and added to addition funnel. The reaction was carried out in 0° C. ice bath with slowly drops of DCC solution and reacted for 24 h. The crude product of macroinitiator was precipitated from diethyl ether and then dried in vacuum oven at room temperature. The dry crude macroinitiator was further purified by ultrafiltration membrane (Millipore MWCO 10K) and then freeze dried. The product was characterized by $^1$H-NMR (Acetone-d6), which is shown in FIG. 3. The polydispersity index (PI) was 1.02 from GPC determination, which is shown in FIG. 4.
Synthesis of N-n-propylacrylamide (NnPAAm) Monomer.

Figure 5:
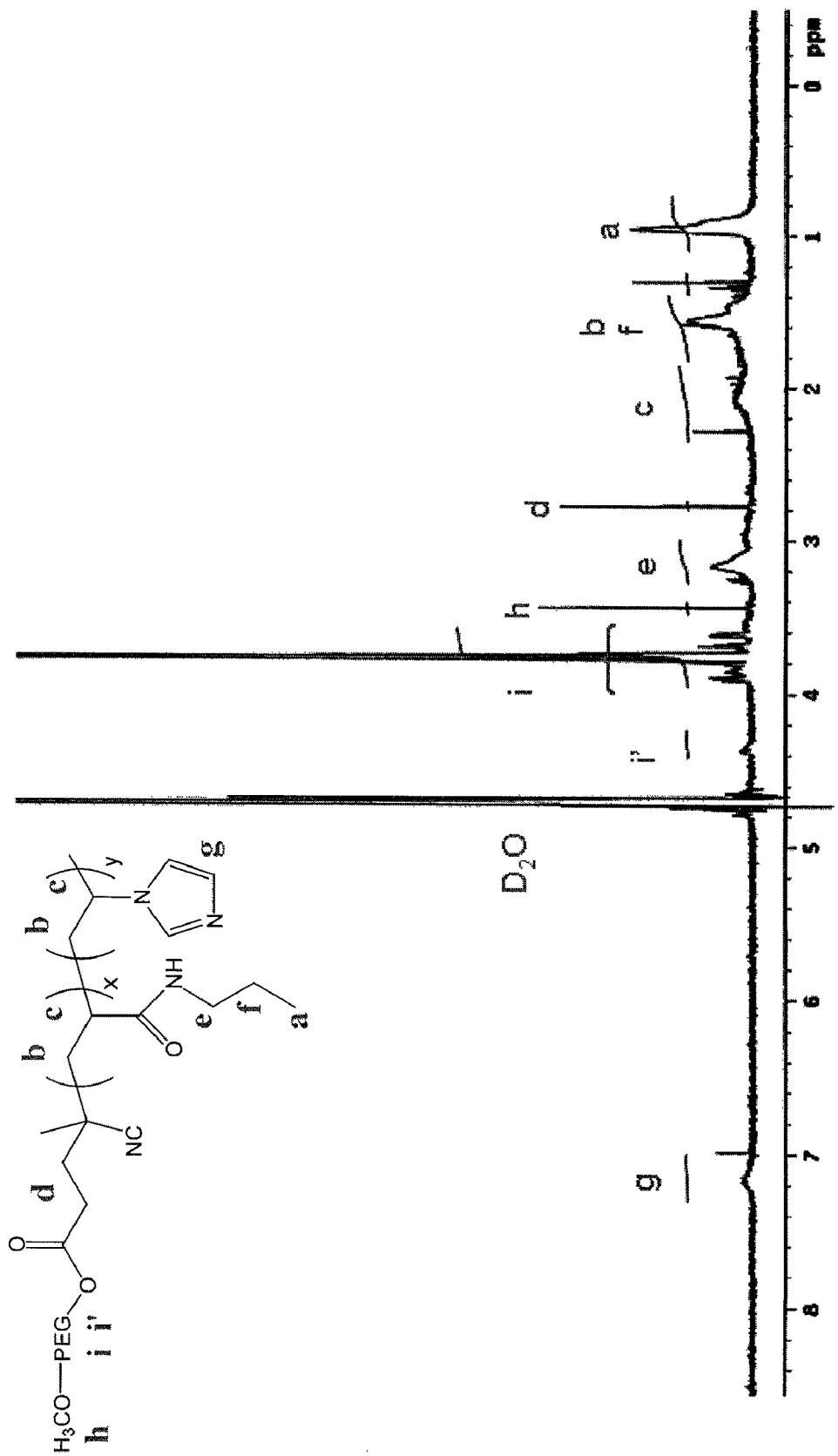
FIG. 5 shows $^1$H-NMR spectrum of mPEG-b-P(NnPAAm-co-VIm) diblock copolymer.

The N-n-propylacrylamide was prepared as follows. N-n-propylamine and triethylamine (molar ratio 1/1) were dissolved in dry toluene and placed in a two-necked flask with a magnetic stirrer and an addition funnel. The solution was then cooled to 0° C. Acryloylchloride (equal molar to N-n-prorylainine) was also dissolved in toluene and added to addition funnel, wherein acryloylchloride solution was added slowly over a period of 2.5 h such that the temperature of the mixture in the flask did not exceed 5° C. The resulting mixture was stirred at 10° C. for 24 h. Following by filtration of triethylamine hydrochloride and distillation of toluene in vacuum at 60° C., the residual product was further purified by distillation in vacuum at 80° C. The products were characterized by 1H-NMR (DMSO-d6).
Synthesis of mPEG-b-P(NnPAAm-co-VIm) Diblock Copolymer.

mPEG-b-P(NnPAAm-co-VIm) diblock copolymer was synthesized by free radical polymerization. NnPAAm, N-vinylimidazole, and mPEG2-ABCPA macroinitiator were dissolved in DMSO, and then placed to a two-necked round-bottle flask with a magnetic stirred. After purging with $N_2$, the reaction was conducted at 70° C. for 24 h under a nitrogen atmosphere. The products were purified by precipitation in diethyl ether and dialysis against Milli-Q water. The product was characterized by $^1$H-NMR (D$_2$O), which is shown in FIG. 5. The polydispersity index (PI) was 1.18 from GPC determination.

Micelles and Mixed Micelles Preparation.

mPEG-b-PLA, mPEG-b-P(NnPAAm-co-VIm), or their mixture were dissolved in 5 ml of acetone. The total weight of copolymers was controlled at 80 mg. The copolymer solution was then dropped into phosphoric acid buffer solution (pH 7.4, I=0.01) at 60° C. with well stir for a period time. The mixture aqueous solution was placed in a rotary evaporator to remove the acetone and was kept at 40° C. to maintain a stable single/mixed micelles. The particle distribution was directly determined by dynamic light scattering (DLS, Zetasizer 3000HS, Malvern). The correlation functions from DLS were analyzed by the constrained regularized CONTIN method.

Differential Scanning Calorimetry (DSC).

DSC measurements of the mixed micelles and diblock copolymer-only micelles were performed with a Seiko SSC/5200-DSC. A temperature range of −20° C.-100° C. was scanned with a heating rate of 2° C./min. The samples were cooled immediately to −20° C. for 10 min after reaching the temperature and were heated again from −20° C.-100° C. at a heating rate of 2° C./min. The midpoints of heat capacity change in the DSC thermal diagram obtained in the second heating run were taken as the glass transition temperature (Tg).

Stabilities of Micelles and Mixed Micelles.

The stabilities of micelles and mixed micelles were determined by DLS. To determine the influence of temperature-sensitive copolymers on micellar stabilities, samples (micelles and mixed micelles in PBS at a concentration of 2 mg/ml) were thermostated from 37° C. to 25° C. The sample was held at each temperature for at least 10 min to enable it to reach equilibrium. To determine the influence of Cmc copolymers on micellar stabilities, samples were suspended in PBS at a concentration of 8 mg/ml and 0.08 mg/ml, respectively, at 37° C. The sample was held at 37° C. for at least 30 min to enable it to reach equilibrium.

Drug Loading and Release.

Doxorubicin (Dox) loaded mixed micelle was also prepared by hot shock protocol and dialysis. The preparation procedure was similar to that of mixed micelle preparation. Dox-HCl (20 mg) was dissolved in 1.5 mL DMSO. mPEG-b-PLA (20 mg) and mPEG-b-P(NnPAAm-co-VIm) (20 mg) together were dissolved in 1.5 mL DMSO. The Dox-HCl solution was mixed with 12 µL of triethylamine to remove hydrochloride. Then, the free base Dox solution was added into polymer solution and stirred at room temperature for 2 h. The mixture solution was dropped into PBS at 60° C. with a magnetic stirred. Then, the resulting mixture was placed into cellulose membrane bag (molecular weight cut-off, 6000-8000; obtained from SpectrumLabs, Inc) and dialyzed against Milli-Q water at 40° C. for 72 h. The Milli-Q water was replaced every 3 h. Sample drying and drug content evaluation were carried out by a procedure in the literature [5,6].

Internalization (Observation by Confocal Laser Scanning Microscopy CLSM).

Dox accumulated in HeLa cells was localized using a Carl Zeiss LSM5 PASCAL confocal laser scanning microscopy (CLSM). The HeLa cells were seeded 1×10$^5$ per well on cover-slides for 24 h and were then treated with free Dox or Dox-mixed micelles. The concentration of Dox was ca. 10 µg/mL. Dox-mixed micelles were washed with PBS to remove untrapped Dox twice before use. After some time, the cells were washed twice with PBS, and then mounted on a slide with 4 wt % paraformaldehyde for CLSM observation. Fluorescence was observed by confocal microscope at 488 nm for excitation and an LP filter of 590 nm for Dox detection.

RESULTS AND DISCUSSION

Figure 6:
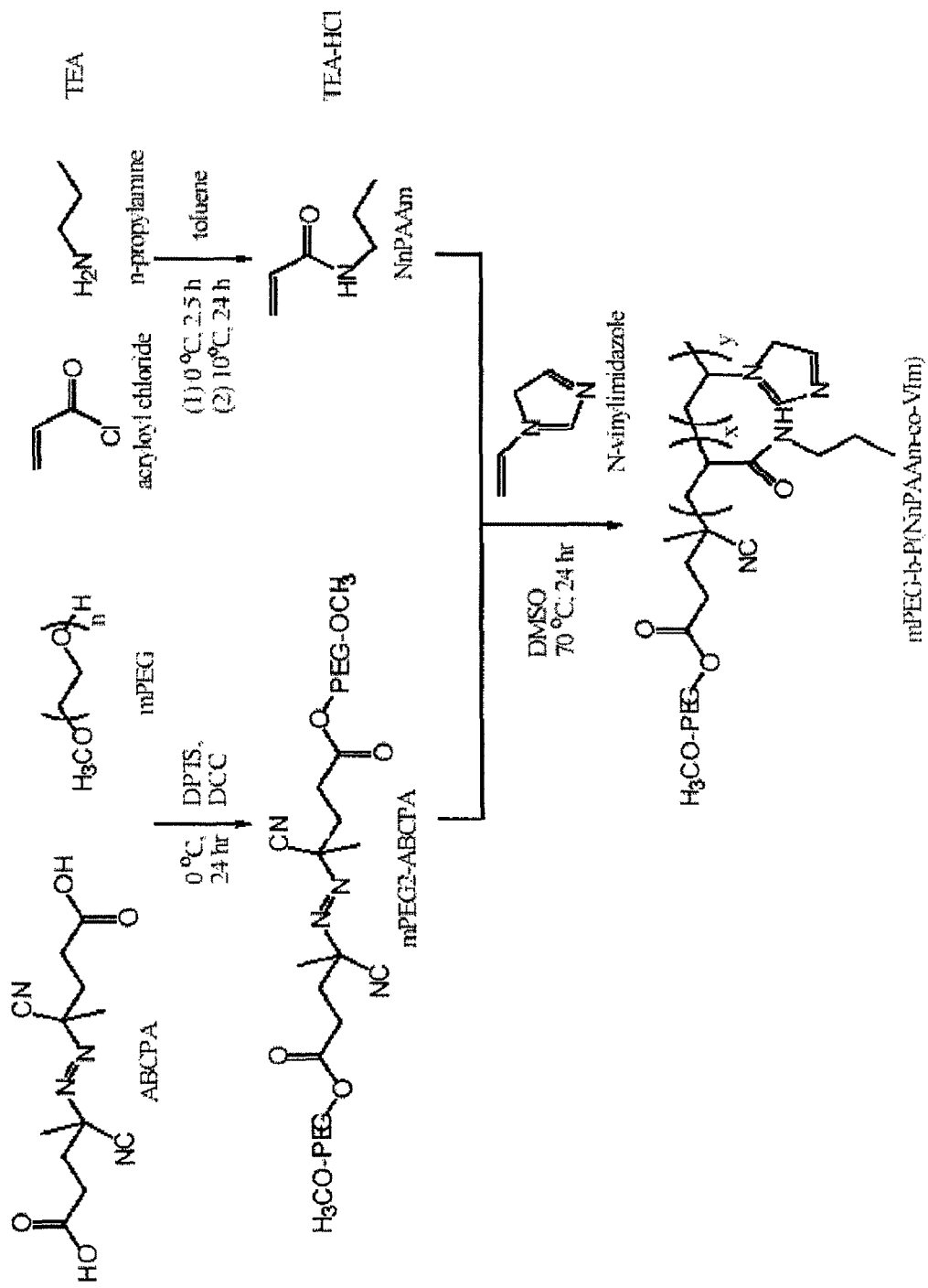
FIG. 6 shows synthesis process and chemical structure of mPEG-b-P(NnPAAm-co-VIm) diblock copolymer.
Figure 7:
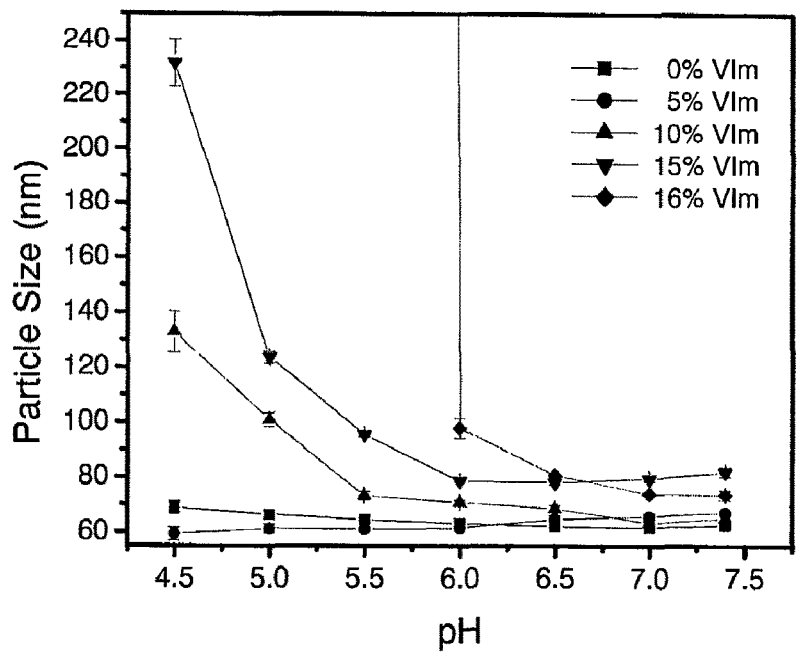
FIG. 7 shows particle sizes of mPEG-b-P(NnPAAm-co-VIm) micelles at various pH at 37° C.
Figure 8:
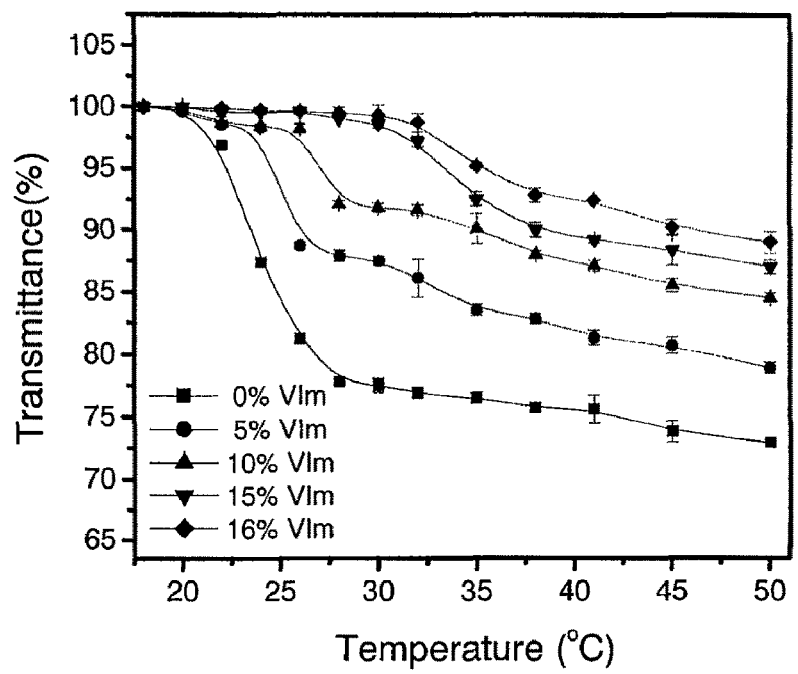
FIG. 8 shows the cloud point of mPEG-b-P(NnPAAm-co-VIm) diblock copolymers.
Figure 9A:
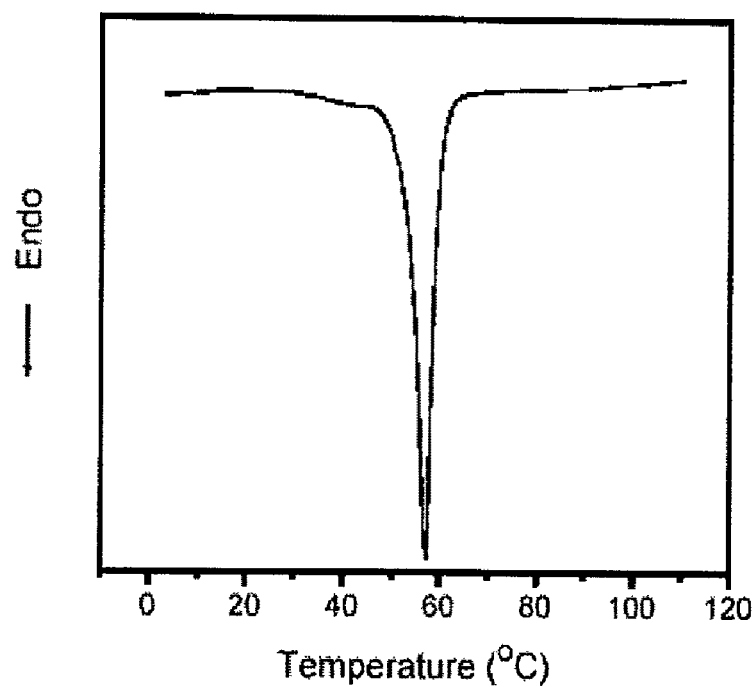
FIGS. 9a, 9b, 9c and 9d show DSC curves of (a) mPEG-b-PLA micelles, (b) mPEG-b-P(NnPAAm-co-VIm) micelles, (c) micelles mixture with equal weight ratio of mPEG-b-P(NnPAAm-co-VIm) and mPEG-b-PLA micelles, and (d) mixed micelles.
Figure 9B:
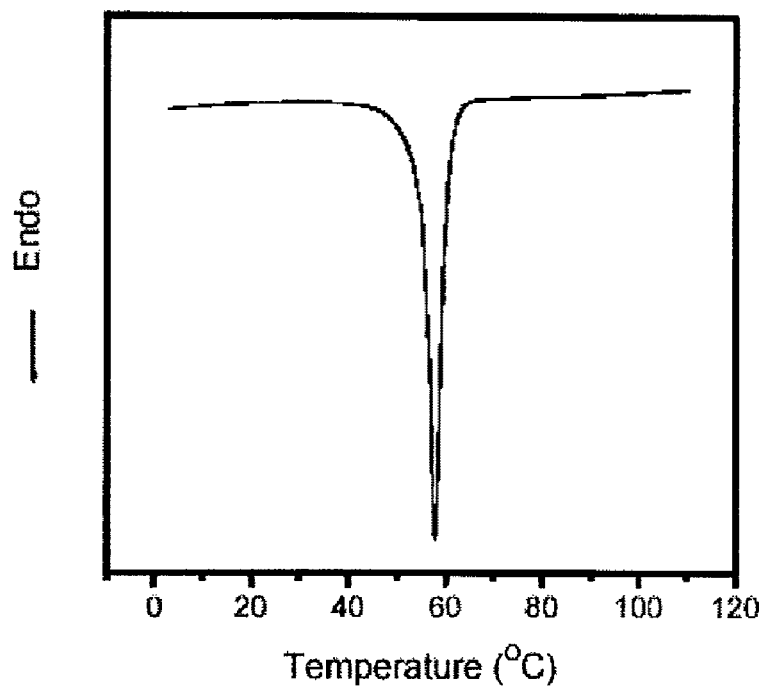
Figure 9C:
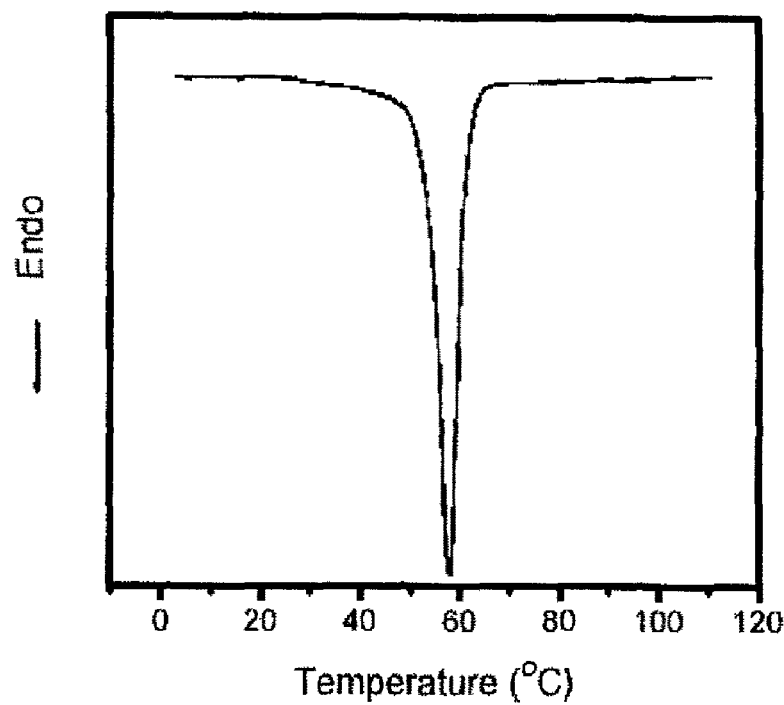
Figure 9D:
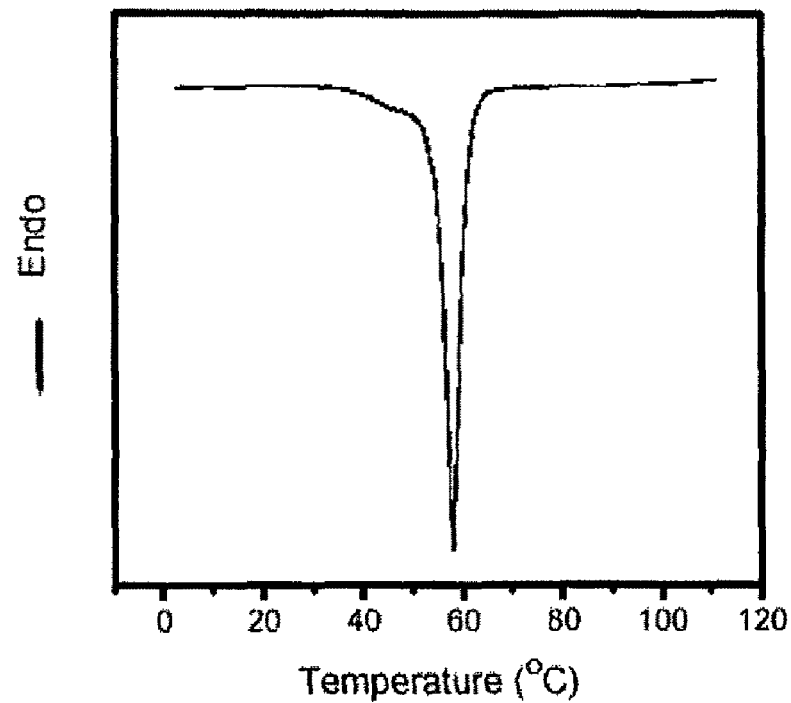

Copolymers.

mPEG-b-PLA diblock copolymer (Mn$^{mPEG}$=5 kg/mol, Mn$^{PLA}$=1.75 kg/mol) was synthesized by ring-opening polymerization. Steady-state fluorescence spectra of the copolymer solutions with a pyrene probe were used to study the Cmc value by a fluorescence spectrophotometer (F-2500, Hitachi). When the pyrene environment changes from polar to nonpolar, the excitation spectra of pyrene are altered, and the peak at 335 nm shifts to 337 or 338 nm as the polymer concentration increases. The Cmc value of mPEG-b-PLA copolymer was determined to be 5.37×10$^{-3}$ mg/mL. The Cmc value is close to a value presented elsewhere for short hydrophobic segments of PLA [21].

mPEG-b-P(NnPAAm-co-VIm) diblock copolymer (Mn$^{mPEG}$=5 kg/mol, Mn$^{P(NnPAAm-co-VIm)}$=1.56 kg/mol) was synthesized by free radical polymerization. mPEG2-ABCPA was used as a macro-initiator. The chemical structures and synthesis process of mPEG-b-P(NnPAAm-co-VIm) diblock copolymer are also shown in FIG. 6. PNnPAAm is similar to poly(N-isopropyl acrylamide) (PNIPAAm), exhibiting an extended chain conformation below the LCST and undergoing an abrupt coil-to-globule transition above its LCST in aqueous solution [22,23]. The LCST of mPEG-b-PNnPAAm in water is about 21.5° C., but can be modulated by copolymerizing with hydrophilic or hydrophobic monomers. Approximately 16 mol % of VIm was introduced into PNnPAAm (calculated from $^1$H-NMR), and the cloud point of mPEG-b-P(NnPAAm-co-VIm) rose in aqueous solution because the VIm molecules disrupted aggregation of NnPAAm and caused mPEG-b-P(NnPAAm-co-VIm) temperature and pH sensitivity due to VIm imidazole group protonation-deprotonation, as shown in FIG. 7 and the following Table 1. The cloud point of mPEG-b-P(NnPAAm-co-Vim) was determined to be around 31° C. by a UV/Vis spectrophotometer (Lambda 2S, Perkim Elmer) at 542 nm. FIG. 8 shows the cloud points of the mPEG-b-P(NnPAAm-co-VIm) listed in Table 1.

TABLE 1

Composition of mPEG-b-P(NnPAAm-co-VIm) diblock copolymers.

| Polymer | Code | In feed (mol %) | | | In copolymer (mol %)$^a$ | | | Mn$^a$ | PDI$^b$ |
|---|---|---|---|---|---|---|---|---|---|
| | | EG | VIm | NnPAAm | EG | VIm | NnPAAm | | |
| mPEG-b- | 0% VIm | 88 | 0 | 12 | 88.1 | 0 | 11.9 | 7490 | 1.20 |
| P(NnPAAm-co-VIm) | 5% VIm | 88 | 0.6 | 11.4 | 87.2 | 0.64 | 12.16 | 7875 | 1.25 |

TABLE 1-continued

Composition of mPEG-b-P(NnPAAm-co-VIm) diblock copolymers.

| Polymer | Code | In feed (mol %) | | | In copolymer (mol %)[a] | | | $Mn^a$ | $PDI^b$ |
|---|---|---|---|---|---|---|---|---|---|
| | | EG | VIm | NnPAAm | EG | VIm | NnPAAm | | |
| | 10% VIm | 88 | 1.2 | 10.8 | 87.8 | 1.21 | 10.92 | 7545 | 1.21 |
| | 15% VIm | 88 | 1.8 | 10.2 | 87 | 1.95 | 11.05 | 7685 | 1.22 |
| | 16% VIm | 88 | 2.4 | 9.6 | 87.1 | 2.08 | 10.82 | 7745 | 1.18 |

[a] Compositions and Mn were calculated from $^1$H-NMR determined.
[b] PDI was determined by GPC (elution solution: DMF).

Micelle Preparation.

Micelles formed with amphiphilic copolymers are generally prepared by ultrasonication or dialysis methods [18,19, 24,25]. In the present invention, however, the Cmc diblock copolymers, mPEG-b-PLA could self-associate to form micelles in aqueous solution at 25° C. and at concentration above its Cmc. On the other hand, the temperature-sensitive diblock copolymers, mPEG-b-P(NnPAAm-co-VIm), still exhibited a random-coil chain under the same conditions because ambient temperature was below its cloud point. Thus, ultrasonication or dialysis methods were not suitable to prepare mixed micelles from a temperature-sensitive diblock copolymer and a Cmc diblock copolymer. In the present invention, the hot shock protocol [26] was used to prepare mixed micelles from mPEG-b-P(NnPAAm-co-VIm) and mPEG-b-PLA. First, equal weight ratios of mPEG-b-PLA and mPEG-b-P(NnPAAm-co-VIm) were dissolved together in acetone, and then dropped into a phosphate buffer saline (PBS, pH 7.4) at 60° C. The temperature (at above their temperature-sensitives) caused P(NnPAAm-co-VIm) segments of mPEG-b-P(NnPAAm-co-VIm) began to aggregate as the copolymer solution intermixed with aqueous solution. Simultaneously, the hydrophobic PLA region of mPEG-b-PLA interpenetrated with mPEG-b-P(NnPAAm-co-VIm) aggregation region to form mixed micelle. Reported in the previous studies from our laboratory [5,6] and others [15], either the temperature-sensitive diblock copolymer or the Cmc diblock copolymer first self-assembled to form micelles while the remaining copolymer was gradually introduced in the micellization process. Thus, the unimers of mPEG-b-P(NnPAAm-co-VIm) and mPEG-b-PLA could participate in the micellization process completely. Data obtained from the dynamic light scattering (DLS) measurement showed that the mixed micelles exhibited mean particle size at 83.7±3.8 nm and a narrow particle size distribution (PI=0.112±0.006). Different weight ratios of mPEG-b-PLA and mPEG-b-P(NnPAAm-co-VIm) were also used for preparing mixed micelles. Particles size distributions were increased by increasing the composition of mPEG-b-PLA diblock copolymer as shown in Table 2. The results are obviously different from previous reports for preparing mixed micelles by dialysis methods [6,27,28], suggesting that the amount of mPEG-PLA in mixed micelles are limited by hot shock protocol for preparing mixed micelles.

TABLE 2

Average diameters and the polydispersity indexes (PIs) of mPEG-b-PLA micelles, mPEG-b-P(NnPAAm-co-VIm) micelles and mixed micelles with different weight ratios of mPEG-b-PLA and mPEG-b-P(NnPAAm-co-VIm).

| Composition (wt/wt %) | | Average | |
|---|---|---|---|
| mPEG-b-PLA | mPEG-b-P (NnPAAm-co-VIm) | diameter (nm) | PI |
| 100 | 0 | 122.2 ± 3.8 | 0.225 ± 0.019 |
| 0 | 100 | 73.5 ± 1.8 | 0.080 ± 0.008 |
| 25 | 75 | 81.9 ± 0.5 | 0.096 ± 0.011 |
| 50 | 50 | 83.7 ± 3.8 | 0.112 ± 0.006 |
| 75 | 25 | 61.0 ± 1.1 | 0.341 ± 0.005 |

Miscibility of Two Copolymers in Micelles.

The miscibility of two types of copolymers in mixed micelles was confirmed by differential scanning calorimetry (DSC). DCS could not only use for determining the miscibility of two polymer blends [29,30], but also appropriate use for investigating the distribution of one component in mixed micelle system [31]. FIGS. 7a, 7b and 7c show the DSC curves of mPEG-b-PLA micelles, mPEG-b-P(NnPAAm-co-VIm) micelles and mixed micelles formed by two copolymers. The weak step in the specific heat of mPEG-b-PLA micelles was observed at 32.6° C., which is the glass transition temperature of PLA. As already reported elsewhere, the glass transition temperature of PLA ranges from 30 to 50° C. as the molecular weight varies [32]. The peaks in the region from 55 to 60° C. correspond to the melting point of mPEG [30]. The glass transition temperature of mPEG-b-PLA micelles was 6.4° C. higher than that of mPEG-b-PLA copolymers, because of the aggregation of PLA which hinders the molecular motion of PLA domains via a binding effect [33]. On the other hand, mPEG-b-P(NnPAAm-co-VIm) micelles did not exhibit any secondary transition but an endotherm transition at around 57.9° C., attributing to mPEG. The glass transition temperature of micelles mixture of mPEG-b-PLA micelles and mPEG-b-P(NnPAAm-co-VIm) micelles with equal weight ratio was similar to that of mPEG-b-PLA micelles, as an explanation for immiscibility of the two micelles. In the case of mixed micelles (FIG. 7d); however, the glass transition (41.9° C.) was higher than that of mPEG-b-PLA micelles. The reason is probably because the molecular motion of PLA in mixed micelles was hindered by the P(NnPAAm-co-VIm) segments, hence, produced closer core than mPEG-b-PLA alone. This result indicated that two copolymers were completely miscible in mixed micelles. That is like the glass transition temperature of the PS domain in $TiO_2$-TMAC/PS-b-PMMA increased because $TiO_2$ aggregated and located in PS domain to hinder the molecular movement of PS [34].

Stabilities of Mixed Micelles.

Figure 10A:
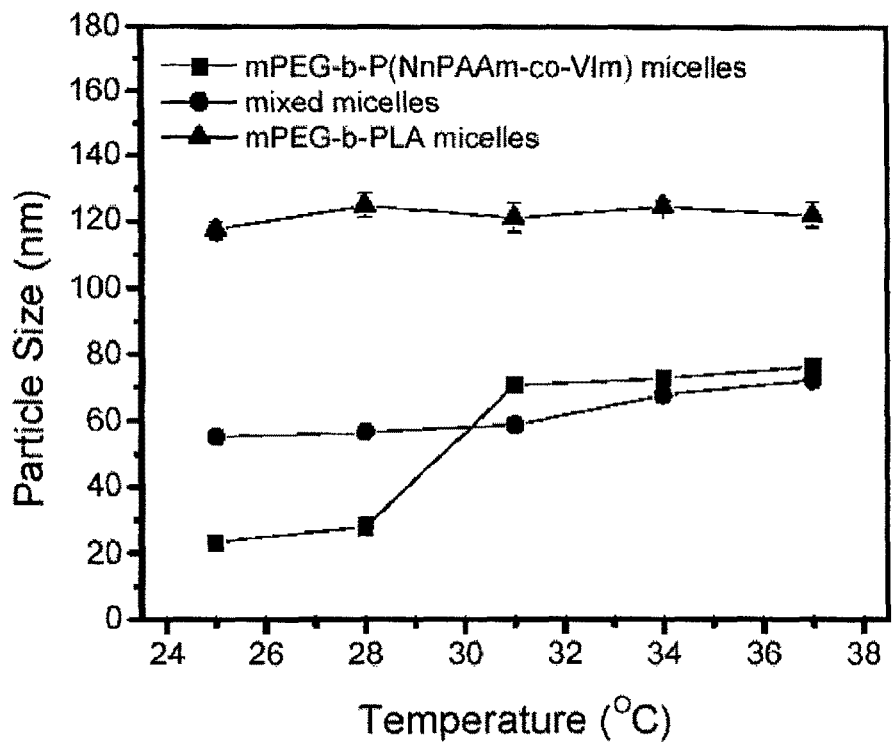
FIGS. 10a to 10d show the stabilities evaluation of mixed micelles, mPEG-b-PLA micelles and mPEG-b-P(NnPAAm-co-VIm) micelles under (a), (b) different temperatures and (c), (d) dilute surroundings by using DLS measurement.
Figure 10B:
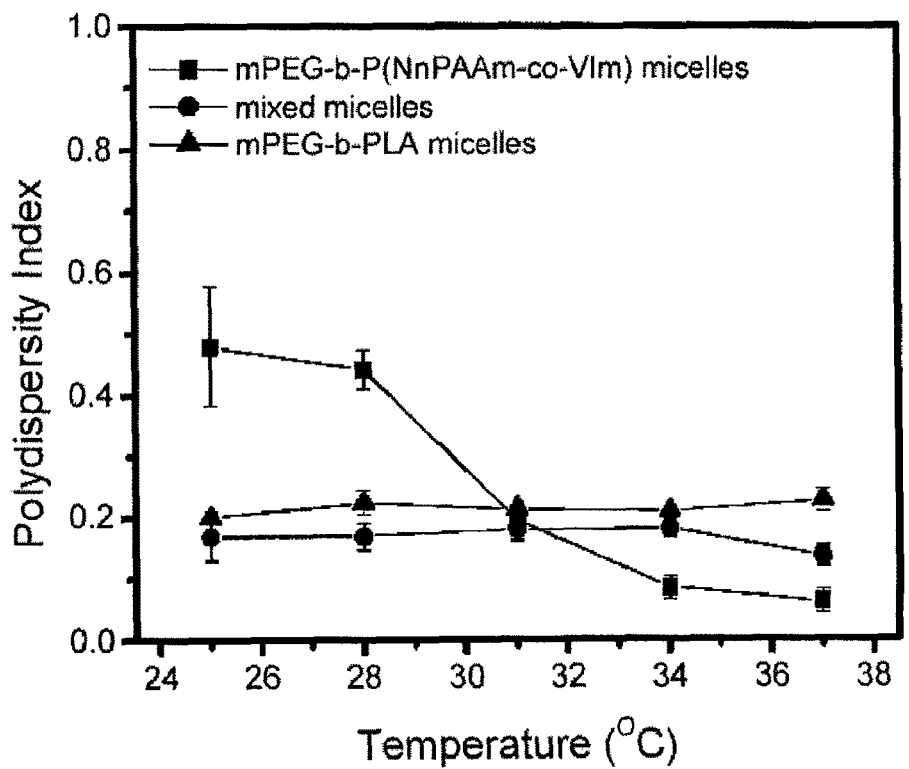

The effect of mPEG-b-PLA in improving stability of the mixed micelles was evaluated by using DLS to observe the changes of the particle sizes in PBS as temperature changed. The results for mPEG-b-P(NnPAAm-co-VIm) micelles and mPEG-b-PLA micelles in PBS were compared. FIG. 10a and FIG. 10b show the particle sizes and polydispersity indices (PIs) of mPEG-b-P(NnPAAm-co-VIm) micelles, mPEG-b-PLA micelles and mixed micelles at the temperature range from 25° C. to 37° C. mPEG-b-P(NnPAAm-co-VIm) micelles decreased their particle sizes and increased PIs from single-distribution to multi-distribution as temperature gradually decreased to below its cloud point. On the contrary, mixed micelles maintained a single peak and a narrow PI as temperature decreased. Results indicated that the mixed micelle structures were stabilized by mPEG-b-PLA diblock copolymers when they presented under low temperature.

Figure 10C:
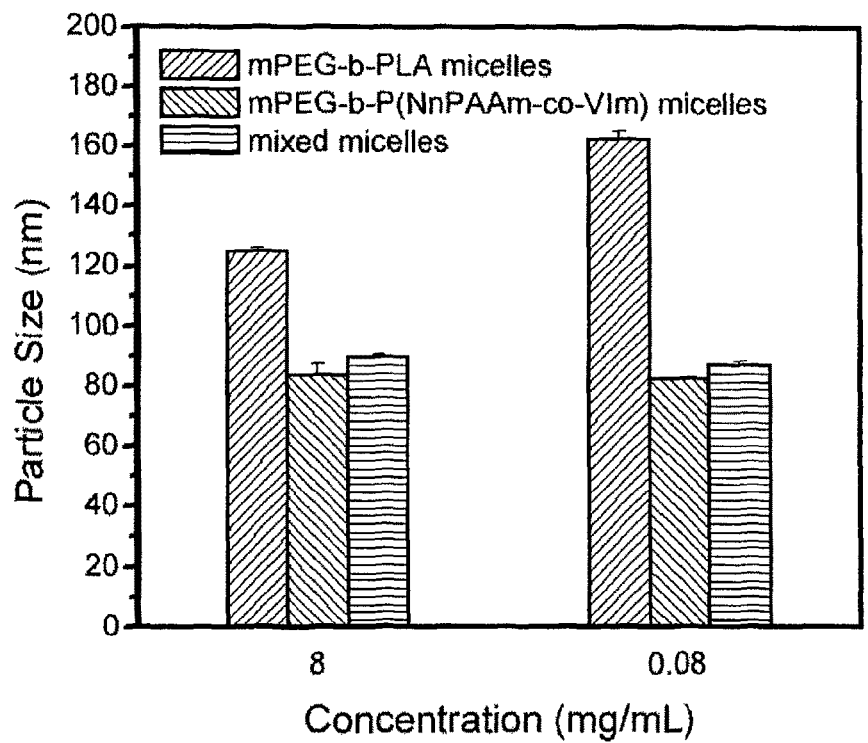
Figure 10D:
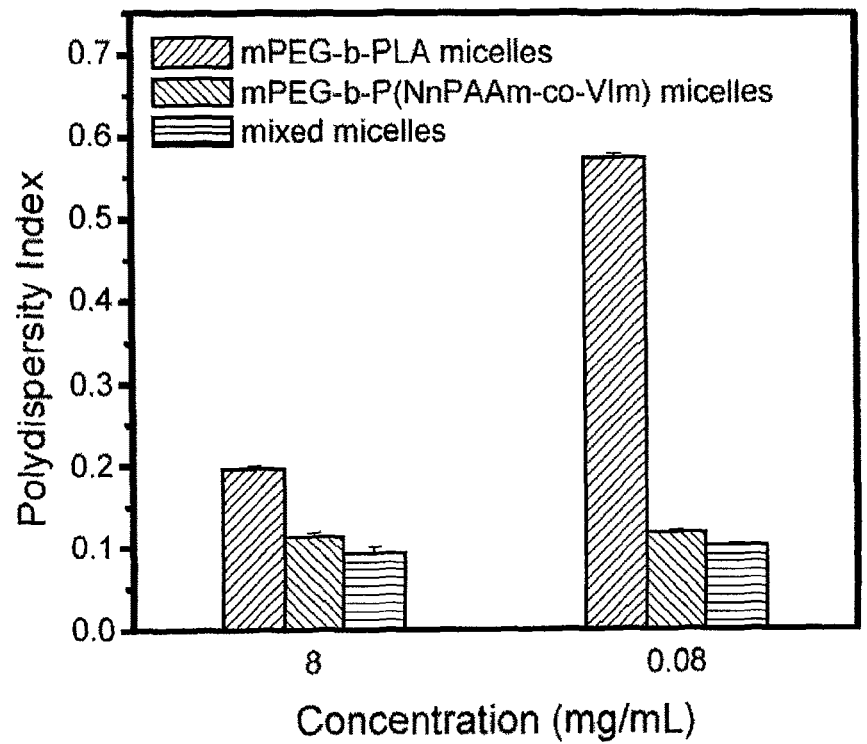

Not only the mPEG-b-PLA copolymers can improve the stability of mPEG-b-P(NnPAAm-co-VIm) micelles at low temperature but also mPEG-b-P(NnPAAm-co-VIm) copolymers can stabilize the mPEG-b-PLA micelles in dilute solution. Because of the characteristics of DLS, micellar solutions were diluted to 0.08 mg/ml to observe their dissociation. FIG. 10c and FIG. 10d show the particle sizes and polydispersity indices (PIs) of mPEG-b-P(NnPAAm-co-VIm) micelles, mPEG-b-PLA micelles and mixed micelles suspended in PBS at concentration of 8 mg/ml and 0.08 mg/ml, respectively, and at the constant temperature of 37° C. Although the concentration of micellar solution of mPEG-b-PLA was above its Cmc, it demonstrated that the mean particle size increased from 124.9±1.1 nm to 162.7±2.3 nm and PI increased from 0.197±0.0306 to 0.573±0.052, when copolymer concentration was diluted from 8 mg/ml to 0.08 mg/ml. It was due to the dissociation of polymer chains on mPEG-b-PLA micelles. It also indicated the instability of mPEG-b-PLA micelles after dilution, especially after intravenous injection into the blood circulation. On the contrary, the mixed micelles maintained their particle sizes and PIs due to the aggregation of P(NnPAAm-co-VIm) segments of mPEG-b-P(NnPAAm-co-VIm) diblock copolymers prohibited the dissociation of mPEG-b-PLA diblock copolymers. The particle sizes of mixed micelles before and after dilution were 89.5 nm and 88.9 nm, and the PIs were 0.09 and 0.10, respectively. Results indicated that the mixed micelle structures were also stabilized by mPEG-b-P(NnPAAm-co-VIm) diblock copolymers when they presented in the dilution process.

pH-Sensitivity.

In addition to investigate a new class of Cmc/temperature-sensitive hybrid mixed micelles, the temperature-sensitive copolymer application in drug delivery with mixed micelle structures is another topic in the present invention. In the case of mPEG-b-P(NnPAAm-co-VIm) diblock copolymers, the Vim molecules was not only increasing the cloud points but also causing copolymers to be prone to pH change due to protonation-deprotonation of the imidazole group of VIm. The effective dissociation constant (pKa) of PVIm is reported to be 6.0 [35]. It is known that during endocytosis a significant drop in the pH value takes place from the physiological value (7.4-7.2) to pH 6.5-5.0 in the endosomes and to around pH 4.5 in primary and secondary lysosomes [36,37]. Through intracellular pH changes, VIms are protonized so to increase the LCST of mPEG-b-P(NnPAAm-co-VIm). Consequently, electrostatic repulsive force arises to dissociate the mixed micelle structure and releases the incorporated drug. On the contrary, the extracellular pH of tumors (ranges from 6.8 to 6.5) is slightly acidic as compared to those of blood and normal tissues [38,39]. As a result, the PolyHistidine (PHis) is protonized in extracellular fluid (pKb of PHis~6.5) [40] so to cause electrostatic repulsive force and micelle swollen. This character might decrease the cumulated amount of micelles in cells. However, mixed micelles containing VIm can remain their size in extracellular fluid to ensure that the endocytosis pathway is processed by cancer cells. Because particles should be smaller than 200 nm for internalizing via coated pits through a non-specific clathrin-dependent process [41].

Figure 11A:
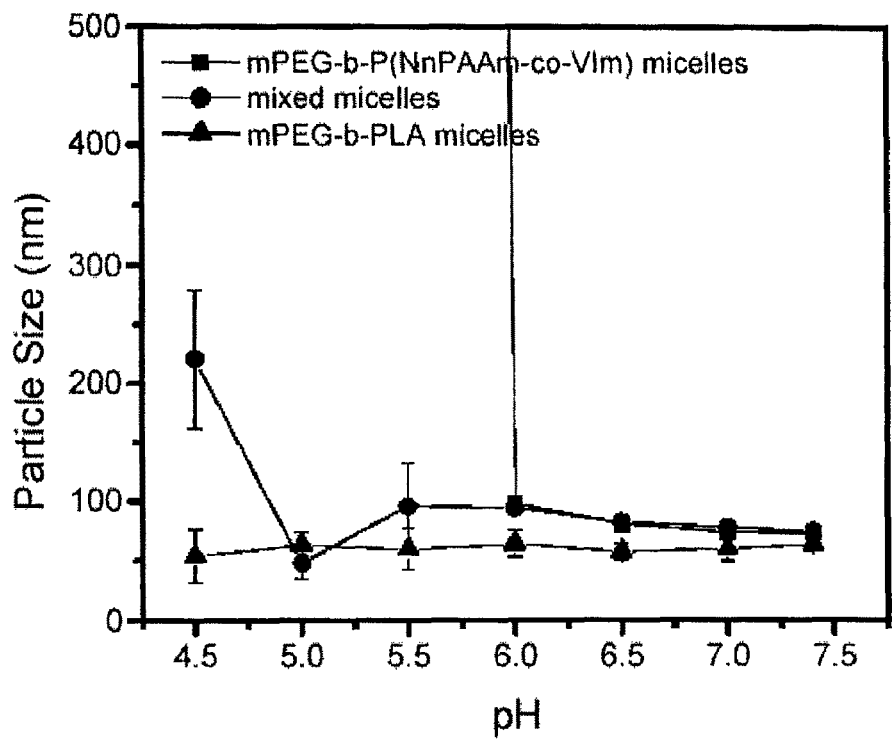
FIGS. 11a and 11b show pH effects on (a) particle sizes and (b) particle size distributions of mPEG-b-P(NnPAAm-co-VIm) micelles, mPEG-b-PLA micelles, and mixed micelles for evaluating the structural changes of micelles. The particle size of mPEG-b-P(NnPAAm-co-VIm) micelles exceeded the detectable maximum when pH was below 6.0. Mean±sd (n=3).
Figure 11B:
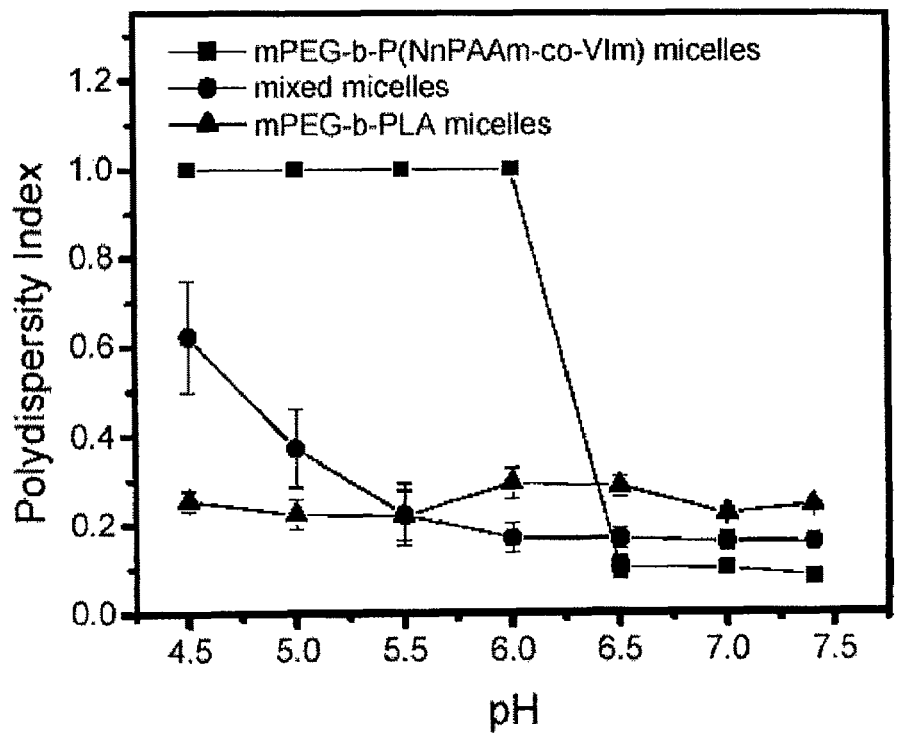

FIGS. 11a and 11b show pH effects on particle size and PI of micelles in different pH buffer solutions as determined by DLS at 37° C., respectively. mPEG-b-PLA micelles, mPEG-b-P(NnPAAm-co-VIm) micelles, and mixed micelles were studied, respectively. When pH was below 6.0, the particle size and PI of mPEG-b-P(NnPAAm-co-VIm) micelles increased rapidly because VIM protonation increased the cloud point of mPEG-b-P(NnPAAmco-VIm) and causeing the repulsion force of P(NnPAAm-co-VIm) segments to dissociate micellar structure. Conversely, mixed micelles maintained its structure above pH 5.5 and sharply increased its particle size and PIs below pH 5.0, indicating that the mPEG-b-P(NnPAAm-co-VIm) was restricted by mPEG-b-PLA to reduce the mobility and repulsion force of VIm as the physiological condition between pH 6.0 and 5.0. By lowering pH below 5.0, the degree of protonation of VIm increases, causing the repulsive force of mPEG-b-P(NnPAAm-co-VIm) stronger than the hydrophobic force of mPEG-b-PLA so to dissociate micellar structure.

Fluorescence spectrometer was also used for determining the structure dissociation of mixed micelles using pyrene as a hydrophobic probe. The pyrene fluorescence spectra experienced large changes due to molecular symmetry reduction in the field surrounding solvent molecules or due to pyrene π-electron cloud distortion caused by environmental perturbation. The ratio $I_1/I_3$, of the first vibrational band intensity to that of the third vibrational band can then be used as an index of environmental polarity [42]. A higher ratio corresponds to more polar surroundings of the pyrene probe [43]. The $I_1/I_3$ of mixed micelles was contrastingly higher below pH 5.5, indicating the structure of mixed micelle changed.

Drug Loading and Release.

To evaluate drug release mechanism, free base doxorubicin (Dox), a hydrophobic anticancer drug was incorporated into mixed micelles through the hot shock protocol. Then, Dox-mixed micelles were prepared by dialysis at 40° C. (above mPEG-b-P(NnPAAm-co-VIm)'s cloud point). All the free Dox was ensured to be completely removed. Based on UV/Vis spectro-photometer analysis [5,19], the drug content was determined to be 32.6 wt %. FIG. 12a shows the TEM images of Dox-mixed micelles stained with $RuO_4$ vapors [44]. It shows that Dox-mixed micelles exhibited a core-shell structure with a mean particle size of 120 nm. Atomic force microscopy (AFM) was used to observe Dox-mixed micelle shapes. FIG. 12b shows uniformly sized Dox-mixed micelles. The diameter was less than that obtained from TEM observation, perhaps because that the high density mixed micelles will shrink and collapse.

Dox released from mixed micelles was isolated from micellar buffer solution by using ultrafiltration membrane (MWCO 10000, Millipore). The pH-response of mPEG-b-P(NnPAAmco-VIm) copolymer with 16 mol % of VIm exhibited more sensitive than that of other mPEG-b-P (NnPAAmco-VIm) copolymers having less amounts of VIm. The drug release profiles exhibited that it possesses good release behavior for future application in mixed micelles. FIG. 13 shows the Dox release kinetics of mPEG-b-PLA micelles, mPEG-b-P(NnPAAm-co-VIm) micelles and mixed micelles at different pH levels. Dox release rates of Dox-mPEG-b-PLA micelles appear to be slightly pH-dependent, because of the presence of the ionizable ammonium group on Dox (pKa~7) [45]. The amorphous polymer, poly(D,L-lactide) served as the core-forming material which allowed Dox to easily diffuse through the polymer matrix [46]. In comparison, Dox-mixed micelles in neutral surroundings (pH 7.4) exhibited an initial burst effect, losing about 10 wt % of Dox at 37° C. Dox release kinetics remained constant after 12 h. However, in the acidic condition (pH~5.0), Dox-mixed micelles exhibited strongly pH-sensitive and released almost 40 wt % of Dox during the initial 24 h at 37° C. This is because imidazole group protonation deformed the micellar structure, releasing Dox from the mixed micelles. Mixed micelle release kinetics in either pH 5.0 or pH 7.4 buffer solutions was also similar to those of the mPEG-b-P(NnPAAm-co-VIm) micelles, indicating that mPEG-b-PLA in mixed micelles only caused slightly structural dissociation.

The time-dependent fluorescence intensity of Dox after Dox-mixed micelles incubated with human cervical epithelioid carcinoma (HeLa) cells was measured with free Dox (Dox-HCl) being used for comparison. The results show that after one hour of incubation, free Dox accumulated in both the nucleus and the cytoplasm. However, a small amount of Dox released from Dox-mixed micelles was observed in the cytoplasm after exposure for 1 hour. Our results indicated that Dox-mixed micelles were taken up from extracellular fluid into cells by endocytosis. Subsequently, the acidic endosomal compartment (ca. pH 5.5-5.0) induced Dox release due to mixed micelle dissociation by VIm protonation. Comparing with other drug delivery systems [47,48], this mixed micelle system shows relative high intensity of Dox in the cytoplasm in the initial 1 h, perhaps due to the different kinds of cell lines or the fast release of the drug from carrier at the initial stage.

Cytotoxicities.

Figure 14A:
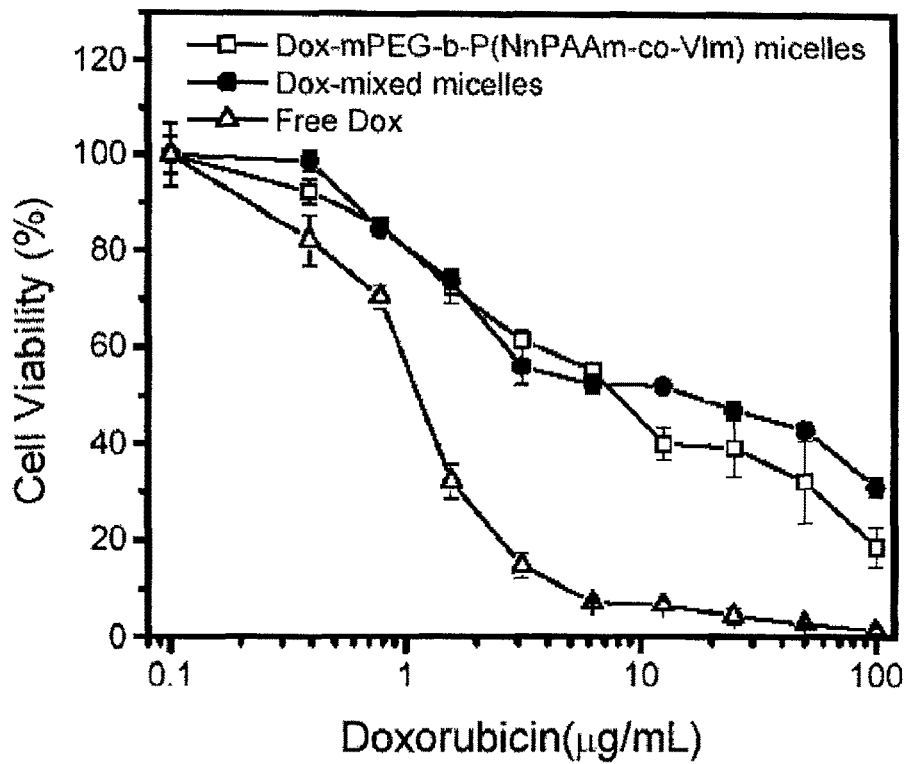
FIGS. 14a and 14b show cell viability of HeLa cells treated with various concentrations of free Dox, Dox-mPEG-b-P (NnPAAm-co-VIm) micelles and Dox-mixed micelles for (a) one day and (b) three day incubation, respectively.
Figure 14B:
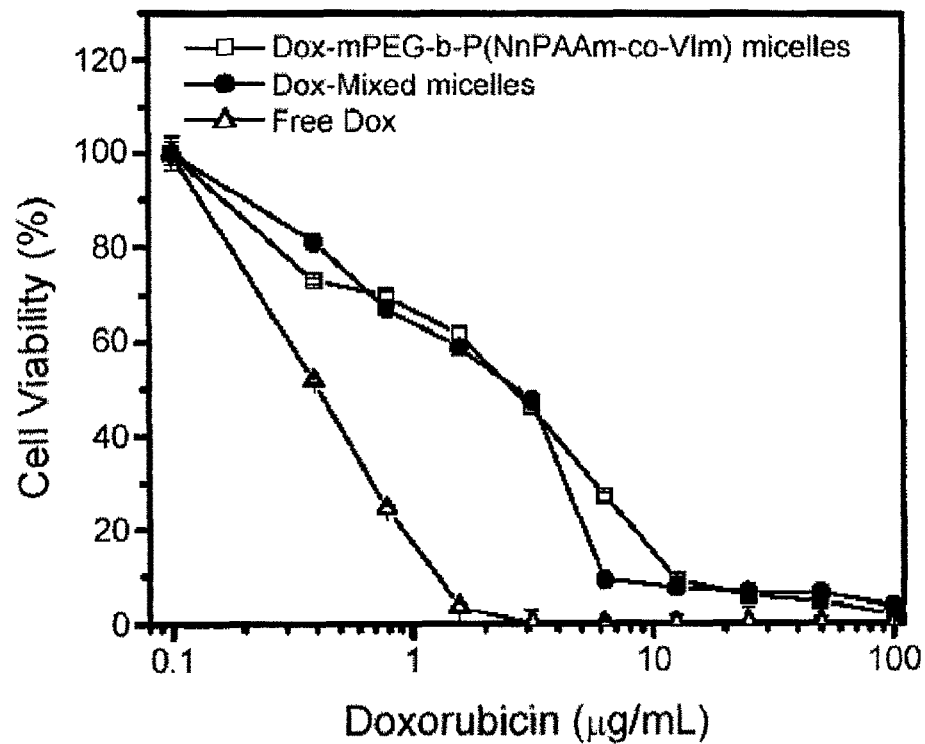
Figure 14C:
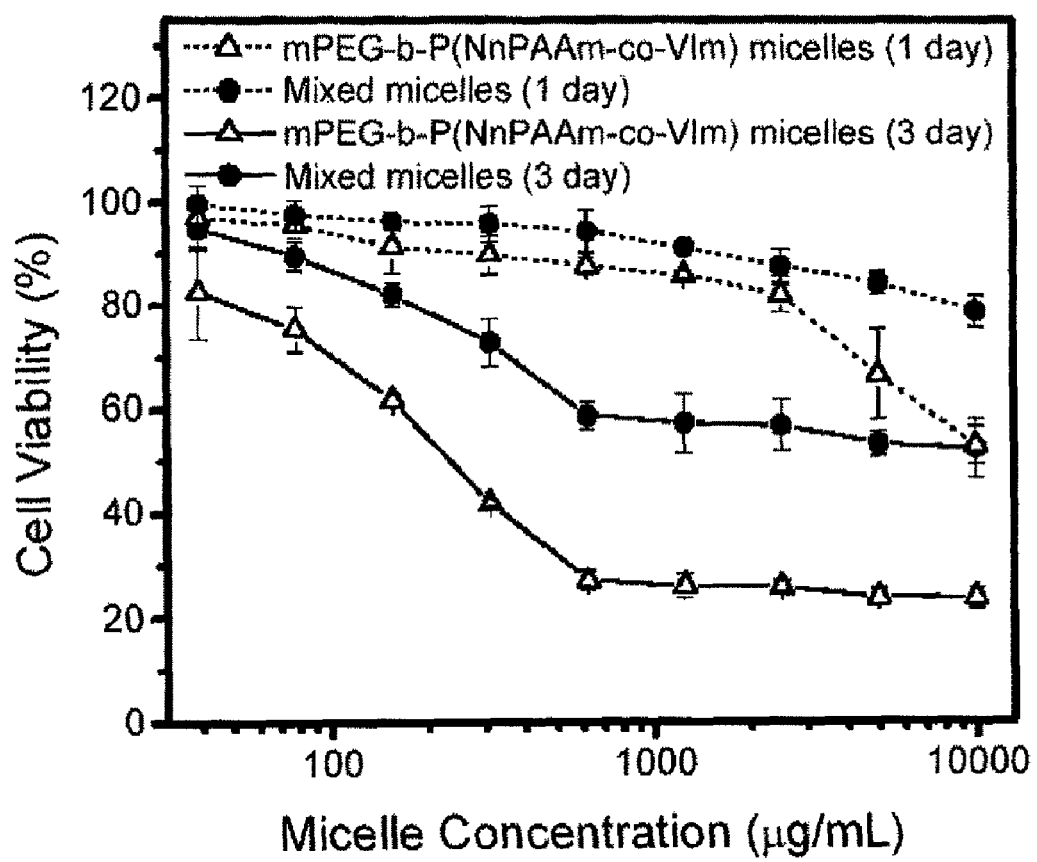
FIG. 14c shows empty micelle cell viability in HeLa cells for one day and three days. Mean±sd (n=6).

The Dox activities of free Dox and Dox-mixed micelles were determined by performing cytotoxicity tests using HeLa cells ($5 \times 10^3$ cell/mL). Cells that survived after incubation were estimated by a tetrazolium dye (MTT) assay [49]. Dox-mPEG-b-P(NnPAAm-co-VIm) micelle was used for comparison. From the results (in FIGS. 14a, 14b and 14c), free Dox exhibited more potent activity than the Dox-mixed micelles and Dox-mPEG-b-P(NnPAAm-co-VIm) micelles, perhaps because Dox cumulative release from mixed micelles or mPEG-b-P(NnPAAm-co-VIm) micelles after 24 h incubation approached 40 wt %. But, when Dox concentration was above 6.25 μg/mL, cytotoxicities of Dox-mixed micelles and Dox-mPEG-b-P(NnPAAm-co-VIm) micelles were close to that of free Dox for the three day incubation, indicating that Dox loaded micelles possessed the same activity as free Dox. The $IC_{50}$ of free Dox and Dox-loaded micelles are summary in Table 3. Direct comparison of cytotoxic potency between other drug delivery systems [50,51] and our mixed micelles imply that our mixed micelles may possess equivalent or higher cytotoxic potency against HeLa cells through a non-specific clathrin-dependent process.

TABLE 3

$IC_{50}$ values of free Dox and Dox-loaded micelles for HeLa cells.

| Code | 24 hrs | 72 hrs |
|---|---|---|
| Free Dox | 2.09 | 0.73 |
| Dox-mPEG-b-P(NnPAAm-co-Vim) micelles | 15.23 | 5.32 |
| Dox-mixed micelles | 24.47 | 4.85 |

Empty mixed micelles and mPEG-b-P(NnPAAm-co-VIm) micelles were also treated with HeLa cells to evaluate material cytotoxicities. The $IC_{50}$ of empty mPEG-b-P(NnPAAm-co-VIm) micelles and empty mixed micelles for the three day incubation were approximately 233 μg/mL and above 10 mg/mL, respectively. Cytotoxicity difference between mPEG-b-P(NnPAAm-co-VIm) micelles and mixed micelles is that mPEG-b-P(NnPAAm-co-VIm) compositional proportion in mixed micelles was slightly less than that in mPEG-b-P(NnPAAm-co-VIm) micelles with the same treatment concentration. Introducing mPEG-b-PLA into the micelle structure not only decreases mPEG-b-P(NIPAAm-co-VIm) quantity, decreases material cytotoxicity with a positive charge (i.e. VIm), but also stabilizes the micellar structure for biomedical use.

4. Conclusions.

In conclusion, our goal here is to show a proof-of-concept: that is, by combining their individual physicochemical properties of a temperature-sensitive diblock copolymer and a Cmc diblock copolymer to greatly improve micellar stability and extending their applications in controlled drug delivery. Although some problems of this kind of mixed micelles still exist, this new micellar system exhibited several remarkable characteristics, including smaller particle size, uniform particle distribution, easy and economic preparation procedure, much improve stability, and rapid stimulus-response. These characteristics are important for both fundamental research and practical applications. Drug release results, cytotoxicity and CLSM observations indicated that this system provided promising applications in intracellular drug delivery.

REFERENCES

1. Burt H M, Zhang X, Toleikis P, Embree L, Hunter W L. Development of copolymers of poly(D,Llactide) and methoxypolyethylene glycol as micellar carriers of paclitaxel. Colloids Surf B 1999;16:161-171.
2. Iijima M, Nagasaki Y, Okano T, Kato M, Kataoka K. Core-polymerized reactive micelles from heterotelechelic amphiphilic block copolymers. Macromolecules 1999;32:1140-1146.
3. Thurmond K B II, Kowalewski T, Wooley K. Water-soluble knedel-like structures: The preparation of shell-cross-linked small particles. J Am Chem Soc 1996;118:7239-7240.
4. Kang N, Perron M E, Prud'Homme R E, Zhang Y, Gaucher G, Leroux J.-C. Stereocomplex block copolymer micelles: Core-shell nanostructures with enhanced stability. Nano lett 2005;5:315-319.
5. Lo C L, Lin K M, Huang C K, Hsiue G H. Self-assembly of a novel micelle structure form graft and diblock copolymers: an example for determined the limit on polyions in drug delivery. Adv Funct Mater 2006;16:2309-2316.
6. Lo C L, Huang C K, Lin K M, Hsiue G H. Mixed micelles formed from graft and diblock copolymers for application in intracellular drug delivery. Biomaterials 2007;28:1225-1235.

7. Hamley I W. Nanotechnology with soft materials. Angew Chem Int Ed 2003;42:1692-1712.
8. Harada A, Kataoka K. Formation of polyion complex micelles in an aqueous milieu from a pair of oppositely-charged block copolymers with poly(ethylene glycol) segments. Macromolecules 1995;28:5294-5299.
9. Kakizawa Y, Harada A, Kataoka K. Glutathione-sensitive stabilization of block copolymer micelles composed of antisense DNA and thiolated poly(ethylene glycol)-block-poly(L-lysine): A potential carrier for systemic delivery of antisense DNA. Biomacromolecules 2001;2:491-497.
10. Discher D E, Eisenberg A. Polymer vesicles. Science 2002;297:967-973.
11. Liu J Q, Zhang Q, Remsen E E, Wooley K L. Nanostructured materials designed for cell binding and transduction. Biomacromolecules 2001;2:362-368.
12. Johnston T P, Miller S C. Inulin disposition following intramuscular administration of an inulin/poloxamer gel matrix. J Parent Sci Technol 1989;43:279-286.
13. Bhardwaj R, Blanchard J. Controlled-release delivery system for the α-MSH analog Melanotan-I using poloxamer 407. J Pharm Sci 1996;85:915-919.
14. Gao Z, Eisenberg A. A model of micellization for block copolymers in solutions. Macromolecules 1993 ;26:7353-7360.
15. Sens P, Marques C M, Joanny J-F. Mixed micelles in a bidisperse solution of diblock copolymers. Macromolecules 1996;29:4880-4890.
16. Honda C, Yamamoto K, Nose T. Comicellization of binary-mixtures of block-copolymers with different block lengths in a selective solvent. Polymer 1996;37:1975-1984.
17. Liu T, Nace T N, Chu B. Self-assembly of mixed amphiphilic triblock copolymers in aqueous solution. Langmuir 1999;15:3109-3117.
18. Lee E S, Na K, Bae Y H. Super pH-sensitive multifunctional polymeric micelle. Nano Lett 2005;5:325-329.
19. Huang C K, Lo C L, Chen H H, Hsiue G H. Multifunctional micelles for cancer cell targeting, distribution imaging, and anticancer drug delivery. Adv Funct Mater 2007; 17:2291-2297.
20. Moore J S, Stupp S I. Room temperature polyesterification. Macromolecules 1990;23:65-70.
21. Hagan S A, Coombes A G A, Garnett M C, Dunn S E, Davies M C, Illum L, et al. Polylactide.poly(ethylene glycol) copolymers as drug delivery systems. 1. characterization of water dispersible micelle-forming systems. Langmuir 1996;12:2153-2161.
22. Ito D, Kubota K. Solution properties and thermal behavior of poly(N-n-propylacrylamide) in water. Macromolecules 1997;30:7828-7834.
23. Maeda Y, Nakamura T, Ikeda I. Changes in the hydration states of poly(N-alkylacrylamide)s during their phase transitions in water observed by FTIR spectroscopy. Macromolecules 2001;34:1391-1399.
24. Lo C L, Lin K M, Hsiue G H. Preparation and characterization of intelligent core-shell nanoparticles based on poly (D,L-lactide)-g-poly(N-isopropyl acrylamide-co-methacrylic acid). J Control Rel 2005;104:477-488.
25. Hsiue G H, Wang C H, Lo C L, Wang C H, Li J P, Yang J L. Enviromental-sensitive micelles based on poly(2-ethyl-2-oxazoline)-b-poly(L-latide) diblock copolymer for application in drug delivery. Int J Pharm 2006;317:69-75.
26. Neradovic D, Soga O, Van Nostrum C F, Hennik W E. The effect of the processing and formulation parameters on the size of nanoparticles based on block copolymers of poly (ethylene glycol) and poly(N-isopropylacrylamide) with and without hydrolytically sensitive groups. Biomaterials 2004;25:2409-2418.
27. Podhajecka K, Stepanek M, Prochazka K, Brown W. Hybrid polymeric micelles with hydrophobic cores and mixed polyelectrolyte/nonelectrolyte shells in aqueous media. 1. Preparation and basic characterization. Langmuir 2001; 17:4240-4244.
28. Konak C, Helmstedt M. Comicellization of diblock and triblock copolymers in selective solvents. Macromolecules 2003;36:4603-4608.
29. Guo M M, Zachmann H G. Structure and properties of naphthalene-containing polyesters. 2. miscibility studies of poly(ethylene naphthalene-2,6-dicarboxylate) with poly(butylene terephthalate) by 13C CP/MAS NMR and DSC. Macromolecules 1997;30:2746-2750.
30. Akiba I, Ohba Y, Akiyama S. Phase structure in blonds of poly(ethylene glycol) and poly(styrene-comethacrylic acid). Macromolecules 1999;32:1175-1179.
31. Ruysschaert T, Sonnen A F P, Haefele T, Meier W, Winterhalter M, Fournier D. Hybride Nanocapsules: interactions of ABA block copolymers with liposomes. J Am Chem Soc 2005;127:6242-6247.
32. Steendam R, van Steenbergen M J, Hennink W E, Frijlink H W, Lerk C F. Effect of molecular weight and glass transition on relaxation and release behaviour of poly(D,L-lactic acid) tablets. J Control Release 2001;70:71-82.
33. Yeh S W, Wei K H, Sun Y S, Jeng U, Liang K S. Morphological transformation of PS-b-PEO diblock copolymer by selectively dispersed colloidal CdS quantum dots. Macromolecules 2003;36:7903-7907.
34. Weng C C, Wei K H. Selective distribution of surface-modified $TiO_2$ nanoparticles in polystyrene-b-poly(Methyl Methacrylate) diblock copolymer. Chem Mater 2003;15: 2936-2941.
35. Overberger C G, Kawakami Y. Esterolytic activity of imidazole-containing polymers. Synthesis and characterization of copoly[1-alkyl-4- or 5-vinylimidazole/4(5)-vinylimidazole] and its catalytic activity in the hydrolysis of p-nitrophenyl acetate. J Polym Sci: Polym Chem Ed 1978; 16:1237-1248.
36. Haag R, Kratz F. Polymer therapeutics: concepts and applications. Angew Chem Int Ed 2006;45:1198-1215.
37. Duncan R. The dawning era of polymer therapeutics. Nature Rev Drug Discov 2003;2:347-360.
38. Engin K, Leeper D B, Cater J R, Thistlethwaite A J, Tupchong L, McFarlane J D. Extracellular Ph distribution in human tumours. Int J Hyperthern 1995;11:211-216.
39. Ojugo A S E, Mesheehy P M J, McIntyre D J O, McCoy C, Stubbs M, Leach M O, et al. Measurement of the extracellular pH of solid tumours in mice by magnetic resonance spectroscopy: a comparison of exogenous (19)F and (31)P probes. NMR Biomed 1999;12:495-504.
40. Lee E S, Shin H J, Na K, Bae Y H. Poly(L-histidine)-PEG block copolymer micelles and pH-induced destabilization. J Control Rel 2003;90:363-374.
41. Simoes S, Pedro P, Duzgunes N, Pedrosa de Lima M C. Cationic liposomes as gene transfer vectors: barrier to successful application in gene therapy. Curr Opin Mol Ther 1999;1:147-157.
42. Kalyanasundaram K, Thomas T K. Environmental effects on vibronic band intensities in pyrene monomer fluorescence and their application in studies of micellar systems. J Am Chem Soc 1997;99:2039-2044.
43. Kjøniksen A L, Nyström B, Tenhu H. Characterisation of thermally controlled chain association in aqueous solutions of poly(N-isopropyl acrylamide)-g-poly(ethylene oxide)-dynamic light scattering. Colloid Surf A: Physicochem Eng Asp 2003;228:75-83.
44. Durant Y G, Sundberg E J, Sundberg D C. Effects of cross-linking on the morphology of structured latex particles. 2. Experimental evidence for lightly cross-linked systems. Macromolecules 1997;30:1028-1032.
45. Burke T G, Morin M J, Sartorelli A C, Lane P E, Tritton T R. Function of the anthracycline amine in membrane binding: Cellular transport and cytotoxicity. Mol Pharm 1987; 31:552-556.
46. Nasongkla N, Bey E, Ren J, Ai H, Khemtong C, Guthi J S, et al. Multifunctional polymeric micelles as cancer-targeted, MRI-ultrasensitive drug delivery systems. Nano Lett 2006;6:2427-2430.
47. Padilla De Jesus O L, Ihre H R, Gagne L, Frechet J M J, Szoka Jr F C. Polyester dendritic systems for drug delivery applications: in vitro and in vivo evaluation. Bioconjugate Chem 2002; 13:453-461.
48. Bae Y, Fukushima S, Harada A, Kataoka K. Design of environment-sensitive supramolecular assemblies for intracellular drug delivery: polymeric micelles that are responsive to intracellular pH change. Angew Chem Int Ed 2003; 42:4640-4643.
49. Mossman B T. In vitro approaches for determining mechanisms of toxicity and carcinogenicity by asbestos in the gastrointestinal and respiratory tract. Environ Health Perspect 1983;53:155-161.
50. Kono K, Kojima C, Hayashi N, Nishisaka E, Kiura K, Watarai S, et al. Preparation and cytotoxic activity of poly (ethylene glycol)-modified poly(amidoamine) dendrimers bearing adriamycin. Biomaterials 2008;29:1664-1675.
51. Lee R J, Low P S. Folate-mediated tumor cell targeting of liposome-entrapped doxorubicin in vitro. Biochim Biophys Acta 1995;1233:134-144.

The invention claimed is:
1. A polymeric micelle comprising a temperature-sensitive block copolymer, said temperature-sensitive block copolymer comprising a hydrophobic polymeric segment and a hydrophilic polymeric segment, wherein said hydrophobic polymeric segment is a copolymer of monomers comprising a pH-/ionic strength sensitive monomer and a temperature-sensitive monomer, wherein the polymeric micelle has a lower critical concentration temperature (LCST) lower than 37° C. at a pH value of 7-8 and has a LCST greater than 37° C. at a pH value of 6 or less than 6; the polymeric micelle has a polydispersity index less than 0.2; and the polymeric micelle forms a micellar solution in water with micellar particle sizes within 50-200 nm, wherein said polymeric micelle further comprising a critical micelle concentration (Cmc) block copolymer, wherein said Cmc block copolymer comprises a hydrophobic polymeric segment, and a hydrophilic polymeric segment, wherein
said pH-/ionic strength sensitive monomer selected from the group consisting of acrylic acid, methacrylic acid, butenedioic acid, amino acid, and vinylimidazole;
said temperature-sensitive monomer is N-isopropyl acrylamide or N-n-propyl acrylamide;
said hydrophilic polymeric segment of the temperature-sensitive block copolymer selected from the group consisting of poly(ether), poly(alkylene oxide), poly(alkylene oxide) with terminal C1-C6 alkyl ether, and poly (2-ethyl-2-oxazoline);
said hydrophilic polymeric segment of the Cmc block copolymer selected from the group consisting of poly (ether), poly(alkylene oxide), poly(alkylene oxide) with terminal C1-C6 alkyl ether, and poly(2-ethyl-2-oxazoline);
the hydrophobic polymer segment of the Cmc block copolymer selected from the group consisting of poly (ester), poly(lactide), poly(lactic acid), and polycaprolactone.
2. The polymeric micelle according to claim 1, wherein said Cmc block copolymer is diblock copolymer, and weight ratio of said temperature-tensitive block copolymer to said Cmc diblock copolymer ranges from 99:1 to 25:75.
3. The polymeric micelle according to claim 2, wherein said Cmc diblock copolymer is methoxy-poly(ethylene glycol)-b-poly(D,L-lactide).
4. The polymeric micelle according to claim 3, wherein said temperature-sensitive block copolymer is methoxy-poly (ethylene glycol)-b-poly(N-n-propyl acrylamide-co-vinylimidazole).
5. The polymeric micelle according to claim 1, wherein said Cmc block copolymer has a Cmc value of $1\times10^{-3}$ to $1\times10^{-6}$ mg/mL.
6. The polymeric micelle according to claim 1, wherein the micelle has a LCST lower than 25° C. at a pH value of 7-8; and the micelle forms a micellar solution in water with particle size within 80-150 nm.
7. The polymeric micelle according to claim 1, wherein said hydrophilic polymeric segment of the Cmc block copolymer is methoxy-poly (ethylene glycol).
8. The polymeric micelle according to claim 1, wherein the hydrophobic polymeric segment of the Cmc block copolymer is bioresorable.
9. The polymeric micelle according to claim 1, wherein the hydrophobic polymer segment of the block copolymer is poly(lactide).
10. The polymeric micelle according to claim 1, wherein said hydrophobic polymeric segment of the Cmc block copolymer has a number-average molecular weight of 500-2500, and said hydrophilic polymeric segment of the Cmc block copolymer has a number-average molecular weight of 2000-20000.
11. The polymeric micelle according to claim 1, wherein the Cmc block copolymer has a terminal functionality connected to an end of the hydrophilic polymeric segment thereof, and said terminal functionality is a ligand able to be bound to a receptor on a surface of a tumor cell, a fluorescence group or a dye.

* * * * *